United States Patent [19]
Thorne et al.

[11] Patent Number: 6,050,976
[45] Date of Patent: Apr. 18, 2000

[54] IN-LINE RETRACTABLE SAFETY CATHETER NEEDLE INSERTION ASSEMBLY

[75] Inventors: David L. Thorne, Kaysville; Roy L. Barrus, West Bountiful; Kendall P. Thorne; Gale H. Thorne, both of Bountiful, all of Utah

[73] Assignee: Specialized Health Products, Inc., Bountiful, Utah

[21] Appl. No.: 09/220,104

[22] Filed: Dec. 23, 1998

[51] Int. Cl.$^7$ .................................................. A61M 25/00
[52] U.S. Cl. ........................................... 604/164; 604/171
[58] Field of Search ................................... 604/164, 167, 604/168, 195, 198, 171, 523

[56] References Cited

U.S. PATENT DOCUMENTS

| | | | |
|---|---|---|---|
| 3,574,306 | 4/1971 | Alden | 128/214.4 |
| 4,676,783 | 6/1987 | Jagger | 604/213 |
| 4,762,516 | 8/1988 | Luther | 604/164 |
| 4,832,696 | 5/1989 | Luther | 604/164 |
| 4,966,591 | 10/1990 | Yuen | 604/192 |
| 5,030,212 | 7/1991 | Rose | 604/263 |
| 5,085,639 | 2/1992 | Ryan | 604/110 |
| 5,088,982 | 2/1992 | Ryan | 604/110 |
| 5,108,376 | 4/1992 | Bonaldo | 604/171 |
| 5,112,311 | 5/1992 | Utterberg | 604/177 |
| 5,120,311 | 6/1992 | Sagstetter | 604/110 |
| 5,120,320 | 6/1992 | Fayngold | 604/177 |
| 5,154,699 | 10/1992 | Ryan | 604/116 |
| 5,176,655 | 1/1993 | Mccormick | 604/198 |

(List continued on next page.)

FOREIGN PATENT DOCUMENTS

| | | | |
|---|---|---|---|
| 0 008 451 | 3/1980 | European Pat. Off. | ........ A61M 25/00 |
| 0 033 207 | 8/1981 | European Pat. Off. | ......... A61M 5/14 |
| 0 443 735 A1 | 8/1991 | European Pat. Off. | ......... A61M 5/32 |
| 0 494 932 B1 | 7/1992 | European Pat. Off. | ......... A61M 5/32 |
| 0 499 077 A1 | 8/1992 | European Pat. Off. | ....... A61M 25/06 |
| 0 499 077 B1 | 8/1992 | European Pat. Off. | ....... A61M 25/06 |
| 0 521 145 B1 | 1/1993 | European Pat. Off. | ......... A61M 5/32 |
| 0 534 000 A2 | 3/1993 | European Pat. Off. | ....... A61M 25/06 |
| 0 534 000 B1 | 3/1993 | European Pat. Off. | ....... A61M 25/06 |
| 0 558 162 A2 | 9/1993 | European Pat. Off. | ....... A61M 25/06 |
| 0 558 162 B1 | 9/1993 | European Pat. Off. | ....... A61M 25/06 |
| 0 566 759 B1 | 10/1993 | European Pat. Off. | ....... A61M 25/06 |
| 0 566 769 A1 | 10/1993 | European Pat. Off. | ....... A61M 25/06 |
| 0 436 646 B1 | 8/1994 | European Pat. Off. | ......... A61M 5/32 |
| 0 615 765 A1 | 9/1994 | European Pat. Off. | ....... A61M 25/06 |
| 0 664 139 A1 | 7/1995 | European Pat. Off. | ....... A61M 25/06 |
| 0 692 277 A2 | 1/1996 | European Pat. Off. | ....... A61M 25/06 |
| 0 745 399 A1 | 12/1996 | European Pat. Off. | ......... A61M 5/14 |
| 0 830 871 A2 | 3/1998 | European Pat. Off. | ....... A61M 25/06 |

*Primary Examiner*—John D. Yasko
*Attorney, Agent, or Firm*—Gale H. Thorne

[57] ABSTRACT

Disclosure of methods and apparatus providing bases for design of compact catheter insertion needle retraction safety devices wherein actuators are displaced away from slender needle sheathing bodies to initiate a needle retraction cycle for safely containing a catheter insertion needle after use. Such actuation guards against inadvertent acts, such as depression of an actuator, which may result in untimely needle retraction. Four embodiments of the instant invention are disclosed. In one embodiment, needle retracting energy is stored as a catheter insertion needle is extended for use and is expended to retract the needle into safe containment. Other embodiments comprise power assist mechanisms which store energy during an initial phase of needle retraction to be used to enhance and assist needle retraction during a needle retraction completing phase. In some embodiments, retraction is facilitated by a pair of rigid, elongated, hingedly interconnected arms which are further pivotally coupled to a needle hub assembly and to a device body such that one arm is rotated approximately 180° to retract the needle a distance greater than the length of the so rotated arm to facilitate retraction actuation. One power assist mechanism comprises a part molded as a distortable member of one of the arms. To realize low cost manufacture, the operating device can be made from as few as two injection molded parts. A readily viewable, blood flash chamber permits early detection of evidence of needle entry into a blood vessel.

21 Claims, 20 Drawing Sheets

U.S. PATENT DOCUMENTS

| | | | |
|---|---|---|---|
| 5,188,611 | 2/1993 | Orgain | 604/192 |
| 5,219,339 | 6/1993 | Saito | 604/198 |
| 5,266,072 | 11/1993 | Utterberg | 604/177 |
| 5,279,588 | 1/1994 | Nicoletti | 604/250 |
| 5,330,438 | 7/1994 | Gollobin | 604/177 |
| 5,350,368 | 9/1994 | Shields | 604/263 |
| 5,354,281 | 10/1994 | Chen | 604/177 |
| 5,385,554 | 1/1995 | Brimhall | 604/168 |
| 5,409,461 | 4/1995 | Steinman | 604/110 |
| 5,433,703 | 7/1995 | Utterberg | 604/52 |
| 5,447,501 | 9/1995 | Karlason | 604/198 |
| 5,498,241 | 3/1996 | Fabozzi | 604/177 |
| 5,501,672 | 3/1996 | Firth | 604/177 |
| 5,501,675 | 3/1996 | Erskine | 604/263 |
| 5,505,711 | 4/1996 | Arakawa | 604/171 |
| 5,520,654 | 5/1996 | Wahlberg | 604/164 |
| 5,549,571 | 8/1996 | Sak | 604/198 |
| 5,562,636 | 10/1996 | Utterberg | 604/263 |
| 5,562,637 | 10/1996 | Utterberg | 604/263 |
| 5,573,510 | 11/1996 | Isaacson | 604/158 |
| 5,690,619 | 11/1997 | Erskine | 604/263 |
| 5,704,914 | 1/1998 | Stocking et al. | 604/164 |
| 5,704,924 | 1/1998 | Utterberg | 604/263 |
| 5,772,638 | 6/1998 | Utterberg | 604/263 |
| 5,779,679 | 7/1998 | Shaw | 604/158 |
| 5,795,339 | 8/1998 | Erskine | 604/264 |
| 5,830,190 | 11/1998 | Howell | 604/168 |

IN-LINE RETRACTABLE SAFETY CATHETER NEEDLE INSERTION ASSEMBLY

FIELD OF INVENTION

The present invention relates to safety products which generally pertain to I.V. catheter insertion devices. Such products are aptly applied for retracting and enclosing a contaminated catheter insertion needle (commonly called a stylette) following percutaneous catheter emplacement. For further protection from contamination, the devices, preferably, are limited to single-use and are disposable.

BACKGROUND AND DESCRIPTION OF RELATED ART

Recognition of all too common occurrences of sickness which sometimes prove fatal due to diseases transmitted by inadvertent needle sticks has resulted in development of a variety of safety catheter needle devices which are used in the areas of I.V. catheters. Such devices comprise devices which utilize distally displaced shields which are projected over a retracted needle following insertion of a catheter and other devices which automatically retract the needle when activated by a button push. Other possibilities for catheter insertion needle safety devices include those devices which blunt the needle following catheter insertion.

Even though safety catheter devices have been in commerce for years, less than half the catheters sold in the United States are safety catheters. The most likely reason for sales of safety catheters remaining in the minority is unit cost. Currently, safety catheters sell for about twice the cost of non-safety catheters. As non-safety catheter use represents a significant source of contaminated needle sticks, one might conclude that a safety catheter which could be fabricated for a cost which is competitive with non-safety catheters would find more ready acceptance in the marketplace than current safety catheters, achieve a greater market share and thereby provide significant value through reduction of inadvertent contaminated needle sticks.

As it is generally considered prudent to leave one hand free to care for a patient, particularly to a wound site from which a needle is being withdrawn, a natural consequence is a need for devices which are operable by a single hand. For this reason, devices which can be operated by a single hand or digit thereof are most often preferred over devices requiring more. Further, ease of manipulating the needle from an inserted position to a retracted position is an important characteristic of a safety device requiring critical attention in conception and design. However, even though manipulation should be easy, needle retraction must not be inadvertent. As a consequence, a preferred device would likely be one which requires a positive action to change a state of a retraction mechanism from one stable state to another when the needle is retracted.

BRIEF SUMMARY AND OBJECTS OF THE INVENTION

In brief summary, this novel invention alleviates all of the known problems related to facile, single handed operation of I.V. catheter insertion needle retracting devices. The inventive concepts and processes inherent in the instant invention are basic to devices which comprise elongated, slender core structure for ease in maneuvering to accomplish ready entry into difficult to access vessels. These devices retract needles into safe confines in line with long needle axes and may have power assisted retraction impelled by memory elements in which energy is stored during an initiation phase of a retraction process. These devices can also permit responsive, early visualization of a "blood flash" as the needle penetrates a blood vessel.

For device cost containment and facile manufacture, all such inventive features of such a catheter insertion device may be incorporated through utilization of a single injection molded catheter needle hub and another single injection molded body part. The body part acts as a handle used for facile needle insertion and holds the hub in slideable confinement. Needle retraction actuation mechanisms are an inherent part of the body. The hub and associated needle may be proximally connected in communicating relationship with tubing and other items which are common to I.V. catheter insertion apparatus.

Preferably, for early determination of access to a blood vessel (seen as a flash of red), a flash chamber is provided as part of the needle hub and is distally disposed at the proximal end of the catheter needle. Contents of the flash chamber are transmitted, to be seen by a practicing clinician, through a translucent portion of a surrounding elongated part of the body in which the hub resides. The flash chamber is so disposed to provide an early visualization of blood as near a needle puncture site as possible.

In all embodiments of the invention, the hub is slidably disposed, but securely contained within the elongated body. In unpowered and power assisted embodiments, the hub is securely, but hingeably affixed to an extendable member of the body which is further affixed to a needle retraction actuator. In the various embodiments, the devices may comprise unpowered needle retraction having all phases of needle retraction being the result of manual action against the actuator, power assisted retraction wherein approximately a latter half of needle retraction is compelled by energy stored in a part which is stressed during an initial portion of the actuation.

To guard against inadvertent needle retraction, actuation is induced by extending the actuator away from the rest of the body and needle hub rather than, as an example, by depression of a release mechanism or in-line displacement. In all embodiments, the bodies and retraction mechanisms are of slender construction, according facile rotation about the long axis of the needle to aid in angulated needle penetration of difficult to access blood vessels.

In all embodiments, the body comprises an elongated cylindrical distal section having a distal orifice from which the needle extends for use in a catheter procedure. A distal portion of the hub may also extend outward from the distal body orifice when the needle is disposed for use. Proximal to the distal orifice, the distal section acts as a shield for the distal, sharpened end of the needle when retracted for safety therein.

In manual retraction and power assisted embodiments, the body part comprises a pair of substantially rigid arms hinged to pivot relative to one another. In one of such embodiments, one of the rigid arms is superiorly disposed relative to the other arm and comprises a distal tab which is used as an actuator. The inter-arm hinge is disposed at distal ends of both arms when the needle is extended for use in a catheter procedure. In the needle extended state, the inferiorly disposed rigid arm is also hingeably affixed, at its proximal end, to a medial site to a base portion of the body. In this state, the superior arm is hinged at a proximal end to a proximal part of the needle hub, thereby permitting the entire body part to be folded into a compact, low silhouette apparatus for easy handling.

To retract the needle into a protective shield afforded by the cylindrical distal section of the body, the distal tab is outwardly and proximally displaced, causing the inferiorly disposed arm to pivot about an angle of substantially 180°, thereby displacing the needle and hub in line with the long axis of the needle approximately twice the distance of the length of the inferiorly disposed arm. During needle retraction, the superiorly disposed arm is angulated away from the rest of the body until the inferiorly disposed arm is orthogonally disposed relative to the body base and then, in a continuing proximally directed motion, reseated against the rest of the body parts as the needle is fully retracted.

For power assist, the superiorly disposed arm comprises a flexible, proximally extending part which is stressed against a portion of the needle hub as the superiorly disposed arm is outwardly displaced. Once the inferiorly disposed arm passes the point of orthogonality, energy stored in the extending part urges the superiorly disposed arm inwardly toward the needle hub and, through the hinged connection, the inferiorly disposed arm to a state of lowest potential energy whereat the inferiorly disposed arm completes the displacement of approximately 180°. In the lowest potential energy state, the needle is fully retracted.

Thus, needle retraction is accomplished by a compact, in-line assembly whereby an actuator tab is rotated outward and proximally from a body to retract a needle hub and associated catheter needle proximally until the needle is safely disposed within the distal segment. The action of retraction displaces the device between its two states of highest stability. The retraction action may be power assisted for facile operation.

Note that force applied in along the long axis of the needle is least effective in displacing the needle when the needle is in the fully extended state and in the fully retracted state due to sine laws which apply to such application of force toward hinged parts. Thus, the most stable states of the device occur when the needle is fully extended and when the needle is fully retracted. Even so, to assure device stability a releasable catch may be provided when the needle is extended for use and a secure catch may be provided to assure needle capture upon retraction. For facile use, the body may comprise a pair of handles, preferably laterally disposed relative to the retraction mechanism.

In another embodiment, one of the rigid arms is also superiorly disposed relative to the other arm when the needle is extended for use. However in this embodiment, the superior/inferior relationship reverses as the needle is retracted.

In the state where the needle is disposed for use in a catheter procedure, the initially inferiorly disposed arm comprises a tab on its proximal end, the tab being used as a needle retraction actuator. To establish needle retracting linkages, a hingeable connection is made between the distal end of the initially inferiorly disposed arm and a proximal part of the needle hub. An inter-arm hinge is disposed proximally relative to the hub connection. The initially superiorly disposed arm comprises a distally disposed hinged connection to a base portion of the body.

In this embodiment, the tab and initially inferiorly disposed arm are pivoted outward from the rest of the body and distally to retract the needle. This arm pivots about an angle of approximately 180° whereupon it is displaced to be in superior relation relative to the other arm when a needle is retracted into the distal segment of the body.

The retraction may be assisted by an elastic member affixed between the initially superiorly disposed arm and the body because this arm is neither displaced nor rotated greater than 90° during needle retraction. As was the case in the earlier disclosed embodiment, energy is stored during an initial phase of needle retraction and then released during a latter phase of needle retraction. Release of energy from the elastic member occurs after the initially inferior arm has passed through a state of orthogonality relative to the body base. This release provides assistance in retracting and, thereby, fully securing the needle and associated sharpened needle tip inside the distal segment of the body. Once the initially inferiorly disposed arm passes the point of orthogonality, energy stored in the extended part urges the superiorly disposed arm and, through the hinged connection, the inferiorly disposed arm to a state of lowest potential energy. In the lowest potential energy state, the needle is fully retracted.

Note, in this embodiment as well, that force applied in line with the long axis of the needle is least effective in displacing the needle when the needle is in the fully extended state and in the fully retracted state due to sine laws which apply to such application of force toward hinged parts. Thus, the most stable states of the device occur when the needle is fully extended and when the needle is fully retracted. Even so, to assure device stability a releasible catch may be provided when the needle is extended for use and a secure catch may be provided to assure needle capture upon retraction. For facile use, the body of this embodiment may also comprise a pair of handles, preferably laterally disposed relative to the direction of retraction of the needle securing mechanism.

Thus, needle retraction is accomplished by a compact, in-line assembly whereby an actuator tab is rotated outward and distally relative to the rest of a body of a needle safety device to retract a needle hub and associated catheter needle proximally until the needle is safely disposed within a distal shielding segment of the body. The action of retraction displaces the device between its two states of highest stability. The retraction action may be power assisted for facile operation.

Accordingly, it is a primary object to provide an easy-to-use, low-cost, low-silhouette catheter needle insertion device which, for safety, permits retraction of a used catheter insertion needle into a housing or shield to protect against inadvertent needle sticks from a contaminated needle tip.

It is an important object to provide such a catheter insertion needle device which may be formed using but two injection molded parts.

It is a very important object to provide a needle retraction actuation mechanism which responds only to a deliberate action to guard against inadvertent and unplanned needle retraction.

It is an object to provide a safety catheter needle retraction device which has states of highest stability when the needle is extended for use and when the needle is retracted for safety and states of lower stability there between.

It is an object to provide a safety catheter needle retraction device which is compact in a vertical direction while the device is used in a catheter procedure.

It is an object to provide a safety catheter needle retraction device which is compact in a transverse direction to permit axial rotation about the long axis of the needle for facile access to difficult to enter blood vessels.

It is an object to provide a safety catheter needle retraction device which affords visualization of a blood flash at the proximal end of the needle as an early indicator of needle entry into a blood vessel.

It is a chief object to provide a safety catheter needle retraction device wherein an actuator retracts the needle substantially in line with the long axis of the needle.

It is a primary object to provide a power assisting safety needle retracting apparatus by which retraction is enhanced by action of energy stored during an initiation of a retraction cycle and released toward the end of the retraction cycle to complement completion of needle cycle.

It is also a primary object to provide a powered needle retraction apparatus by which retraction is powered by energy stored while the needle is extended for use.

It is an object to provide a safety catheter needle device comprising retraction powering parts which are maintained in an unstressed state prior to a needle being extended for use, which store energy for retraction as the needle is extended for use and which release the energy to retract the needle only upon deliberate displacement of an actuator.

It is an object to provide a safety catheter needle device having retraction power assisting parts which are maintained in an unstressed state during manufacture and storage and which are stressed to store energy during an early phase of needle retraction actuation and are disposed to release that energy to assist needle motion during a final phase of needle retraction.

These and other objects and features of the present invention will be apparent from the detailed description taken with reference to accompanying drawings.

DETAILED DESCRIPTION OF THE ILLUSTRATED EMBODIMENTS

Unless otherwise specified in this description, the term proximal is used to indicate that segment of a device relatively close to a clinical user of the device. The term distal refers to the segments which are relatively far from the clinical user. Reference is now made to the embodiments illustrated in FIGS. 1–22 wherein like numerals are used to designate like parts throughout. In those cases where a second part performs a function similar to that of a first part, but is different in structure relative to the first part, a prime of the number assigned to the first part may be used. Reference is now made to FIGS. 1–14, which apply to one embodiment of the invention.

Figure 1:
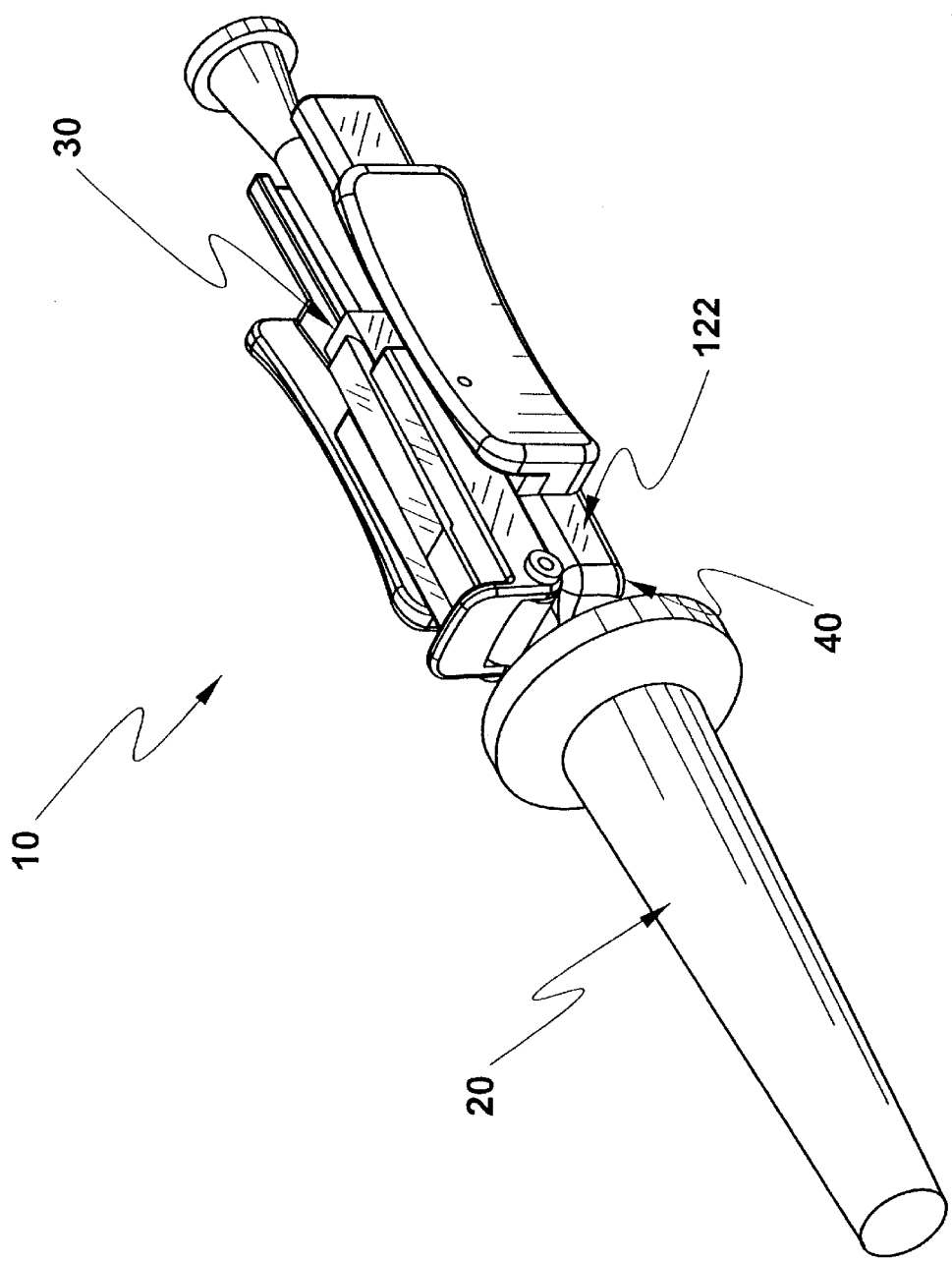
FIG. 1 is a perspective of an embodiment of the invention wherein a catheter insertion needle and associated catheter is disposed within a protective cap.

As seen in FIG. 1, this embodiment, generally referenced as device 10, comprises a needle cap 20, a needle hub assembly 30 and a body assembly 40. Device 10 would normally be provided in a package, such as a "bubble pack" to assure sterility at time of use, but is not shown as such packaging is common in contemporary medical device distribution. Body assembly 40 comprises an elongated, cylindrical distal segment 50, which is seen in part in FIG. 2 and more clearly seen in FIGS. 4 and 5, to which needle cap 20 is releasibly affixed.

Figure 2:
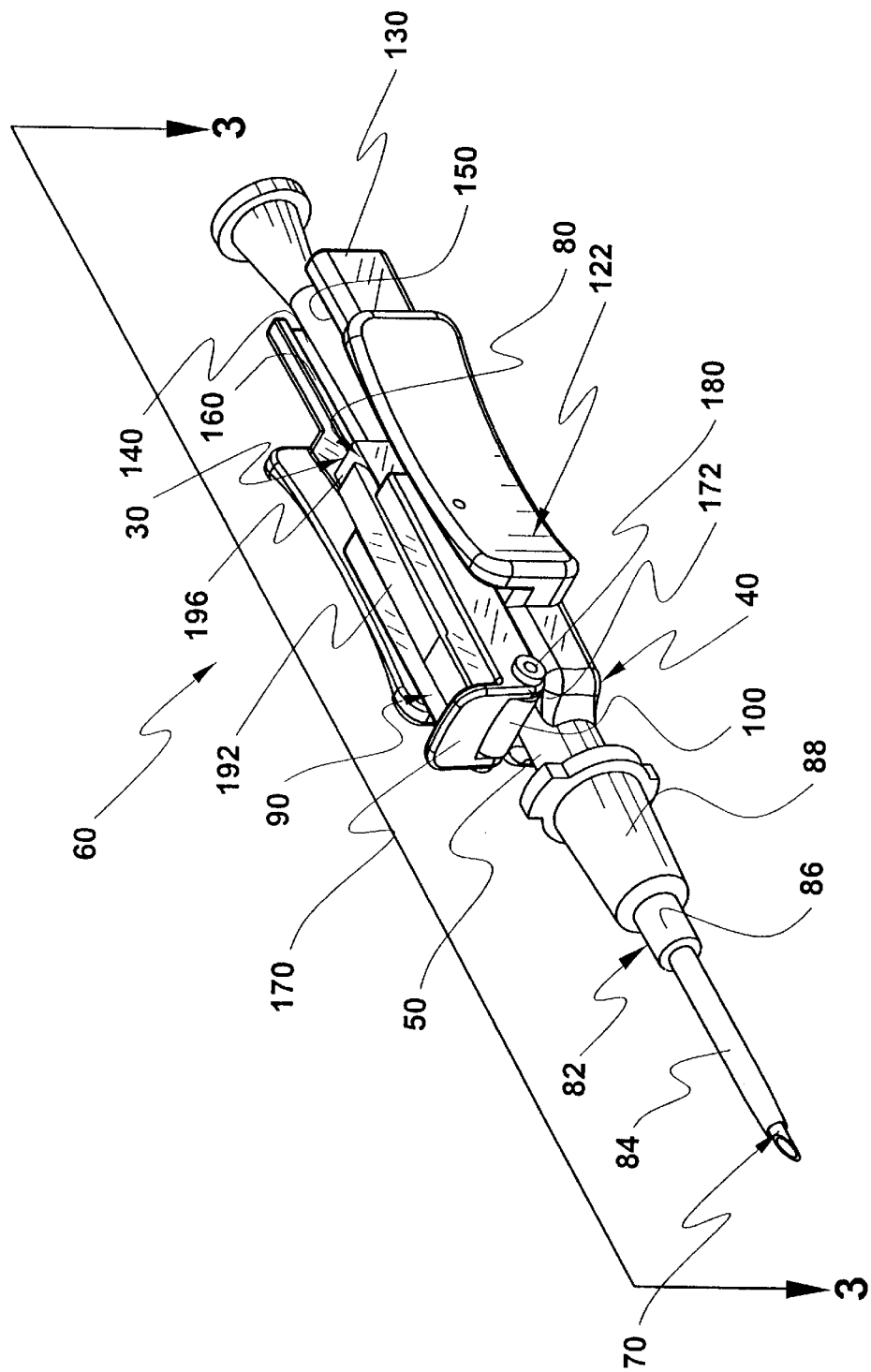
FIG. 2 is a perspective of the embodiment seen in FIG. 1 with the cap removed so that the catheter insertion needle and associated catheter may be seen.

Device 10 with needle cap 20 removed is referenced as device 60, as seen in FIG. 2. In FIG. 2, device 60 is seen to further comprise a hollow bore catheter needle 70 which is a part of needle hub assembly 30 and is securely affixed in a needle hub 80. Disposed about catheter insertion needle 70 for assistance in percutaneous insertion is a catheter assembly, or simply catheter, 82. Catheter assembly 82 comprises a catheter part 84, a catheter hub 86 and a connector 88. Of course, the primary objective for use of device 60 is percutaneous insertion of catheter part 84. Once catheter part 84 is disposed within a vessel of a patient, generally providing fluid access thereto, catheter insertion needle 70 and the rest of device 60 may be removed and properly disposed of. Of course, it is particularly important that needle 70 be safely secured to eliminate any probability of causing an inadvertent needle stick after removal from the patient. Connector 88 is preferably a luer fitting to facilitate attaching medical fluid communicating lines for use of catheter assembly 82 in a medical procedure.

Body assembly 40 comprises a superiorly disposed arm 90, an inferiorly disposed arm 100 and a body base part 122. Body base part 122, seen with other body base parts removed in FIG. 11, comprises an elongated planar base section 120, which is contiguous with two opposing sides 130 and 140 which are essentially orthogonal to base section 120. Side 130 comprises an inwardly extending lip 150. In similar fashion, side 140 comprises an inwardly extending lip 160. In combination, base section 120 and sides 130 and 140 with lips 150 and 160, respectively, combine to form a "U" shaped channel 110. So formed, "U" shaped channel 110 securely maintains hub assembly 30 in slidable containment as catheter insertion needle 70 is retracted from an extended state where it had been used in a catheter procedure to a retracted state where catheter insertion needle 70, or at least its sharpened tip, is enclosed for safety within distal segment 50.

Referring once more to FIG. 2, arm 90 comprises an actuator tab 170 and is affixed at distal end 172 to arm 100 by a hinge 180. As is better seen in FIG. 3, two other hinges which affix arm 90 to hub assembly 30 and arm 100 to body base part 122 are hinges 182 and 184, respectively. Note that base section 120 may be thickened proximally to permit needle 70 to facilely angulate toward a percutaneous entry site when resting upon a patient's skin surface.

Needle 70 is securely affixed in needle hub 80 commonly by adhesive, as is well known in contemporary medical device manufacture. Note that, between a proximal end 186 of needle 70 and actuator tab 170, there is a space where a blood flash may be viewed in a region indicated by number 188. For this reason, material used in body base part 122 and hub 80 must be sufficiently translucent for the blood path to be clearly seen.

Figure 3:
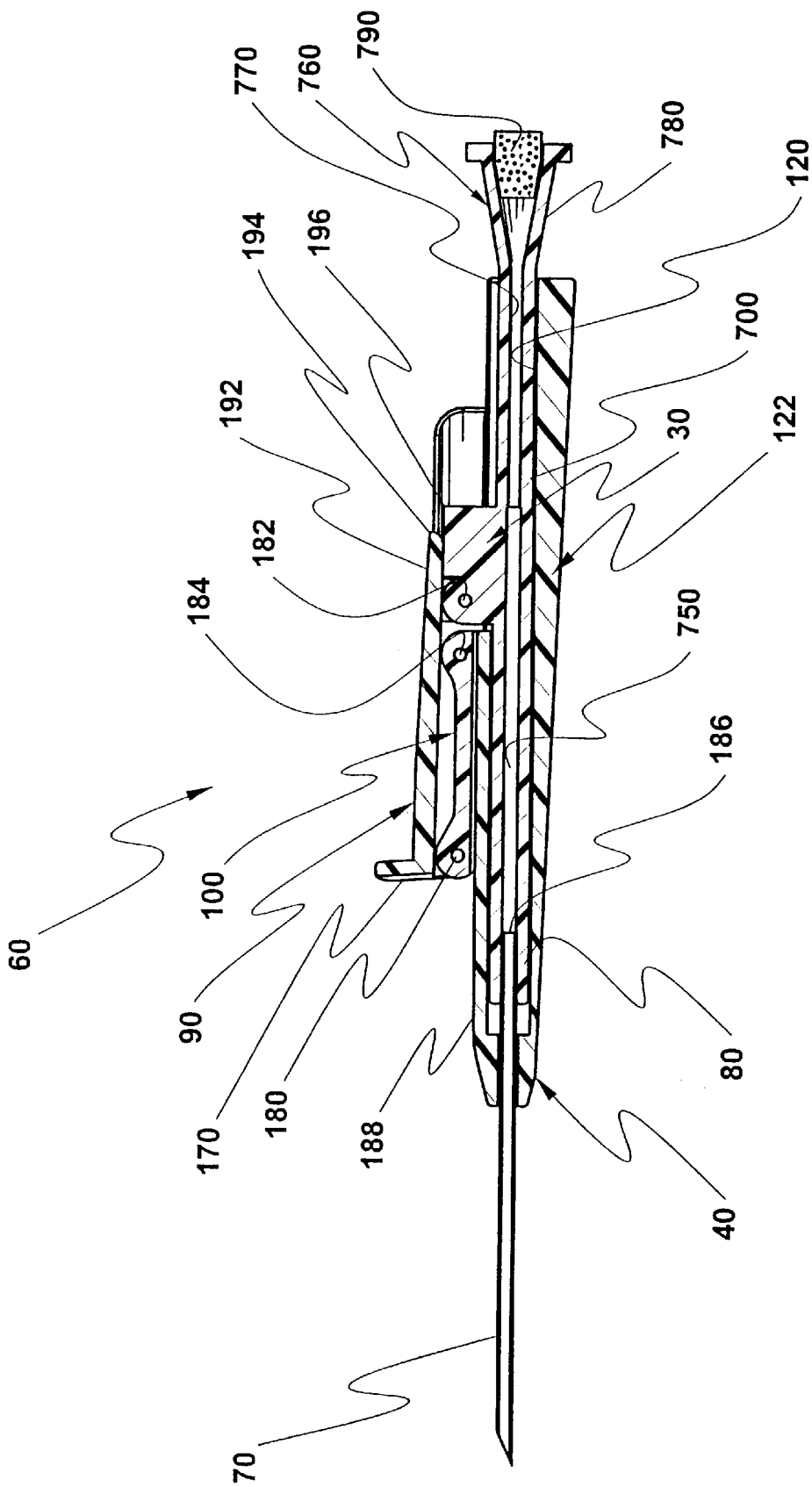
FIG. 3 is a side elevation cross section along lines 3—3 seen in FIG. 2, with the catheter removed.
Figure 4:
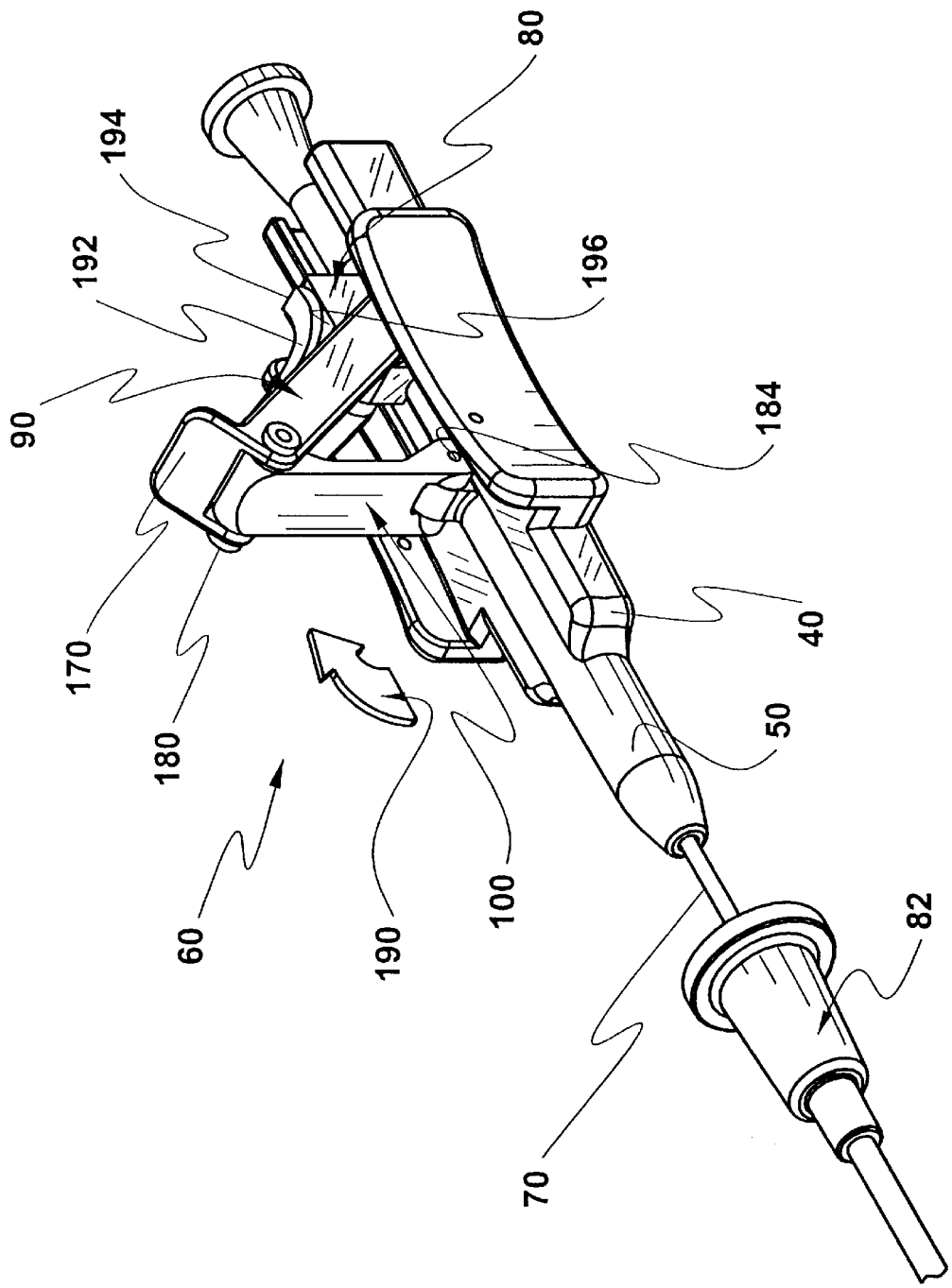
FIG. 4 is a perspective of the embodiment seen in FIGS. 1, 2 and 3, but having the needle displaced proximally and partially retracted by proximal displacement of a needle hub and the catheter displaced distally.

An intermediate state of device 60 while retracting needle 70 is seen in FIG. 4. Application of proximally and outwardly directed force against tab 170 and arm 90, generally in the direction of arrow 190, causes arm 90 to pivot about hinge 182 displacing tab 170 and arm 90 outwardly from the rest of body assembly 40. Through action at hinges 180 and 184, arm 100 is pivoted in a clockwise manner. Further, arm 90 comprises a reluctantly flexible elongated, medially disposed shaft 192 which is generally in a relaxed state as seen in FIGS. 2 and 3. A proximal end 194 of shaft 192 is juxtaposed atop smooth surface 196 of needle hub 80. Displacing arm 90, as seen in FIG. 4, causes shaft 192 to be elastically distorted thereby storing energy therein. The stored energy is directed toward returning arm 90 to a substantially parallel disposition relative to its original state. For this reason, when arm 100 passes through an orthogonal relationship relative to base section 120, the energy stored in shaft 192 forces arm 90 inwardly relative to base section 120 and, as a result, causes arm 100 to further pivot toward base section 120 to, thereby, assist retraction of needle 70. In this manner, with appropriate spring tension physically attributed to shaft 192, pivoting arm 100 just past a point of orthogonality relative to base section 120 permits completion of needle retraction without application of additional force.

It may be preferred to have the spring tension in shaft 192 produce a predetermined force during the completion of needle retraction. As an example, if it is desired to have a relatively constant return force applied through shaft 192 during the completion of needle retraction, a predetermined contour of surface 196 may be used to accomplish a controlled displacement of shaft 192 in the generation of the return force. If shaft 192 is designed such that the spring force in shaft 192, resulting from angular displacement of shaft 192 from the rest of arm 90 ($\alpha$), is proportional to the angular displacement of arm 90 from base section 120 ($\theta$), then, $\alpha = k * \theta$, where k is a spring constant which is dependent upon material and design characteristics of arm 90 and its shaft 192. Further, defining the length of shaft 192 from its free end to a point of connection with the rest of arm 90 is denoted by "L" and the length of a portion of arm 90 from hinge 182 to the point of connection of shaft 192 is denoted by "r", permits a geometric relationship to be established between a rotating arm 90 and shaft 192, as shaft 192 is constrained by contact with surface 196. Note that departure of surface 196 from a plane to one of variable contour causes a related variable force to be imposed upon shaft 192 and therefore upon arm 90 as shaft 192 is displaced along surface 196. So considered, formulae which describe the contour of surface 196 are:

$$y = r \sin\theta - L \sin(1-k)\Theta$$

$$x = L \cos(1-k)\Theta - r \cos\theta$$

where:

y is a vertical distance measured from the surface of initial or at rest contact between shaft 192 and surface 196 and X is a distance, parallel to the top of base section 120, from hinge 182 to the contact point between shaft 192 and surface 196.

Figure 5:
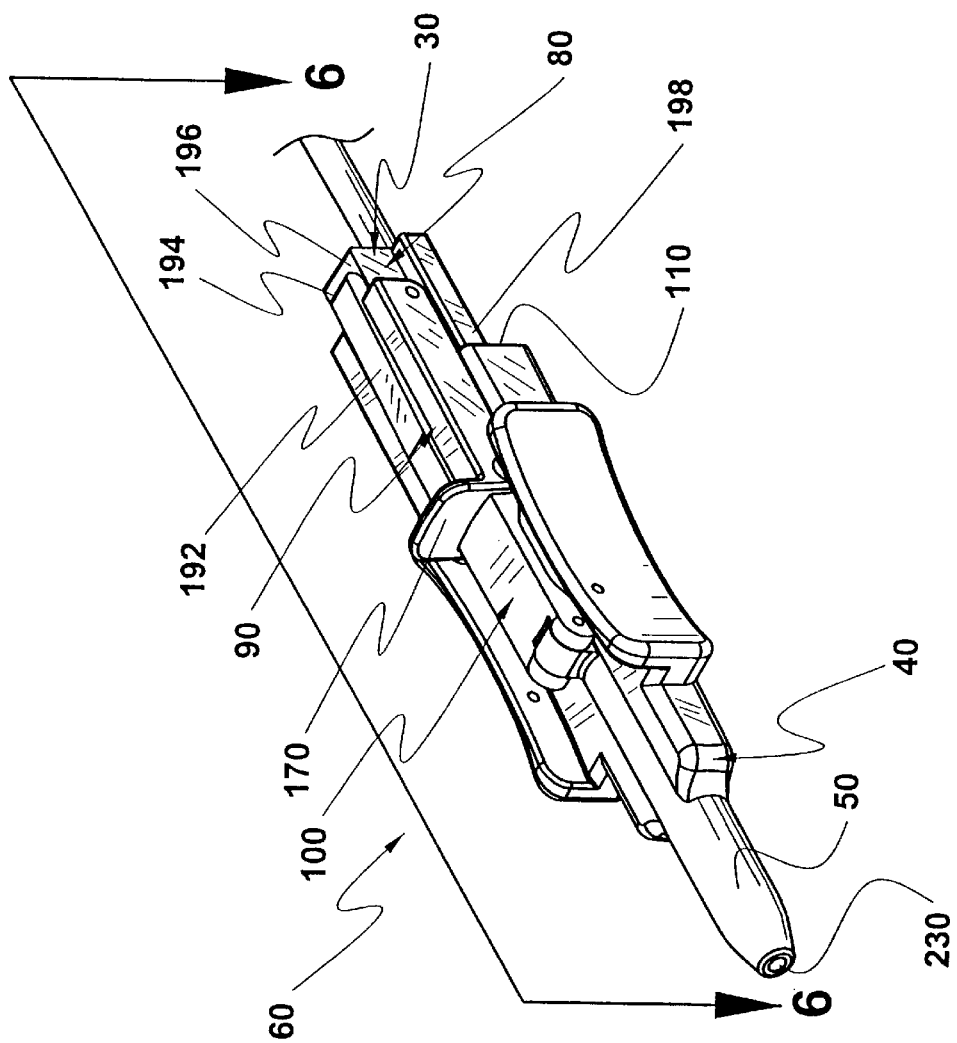
FIG. 5 is a perspective of the embodiment seen in FIGS. 1, 2, 3 and 4 wherein the needle is fully retracted and catheter completely separated from the rest of the embodiment; a portion of the needle hub is truncated.
Figure 6:
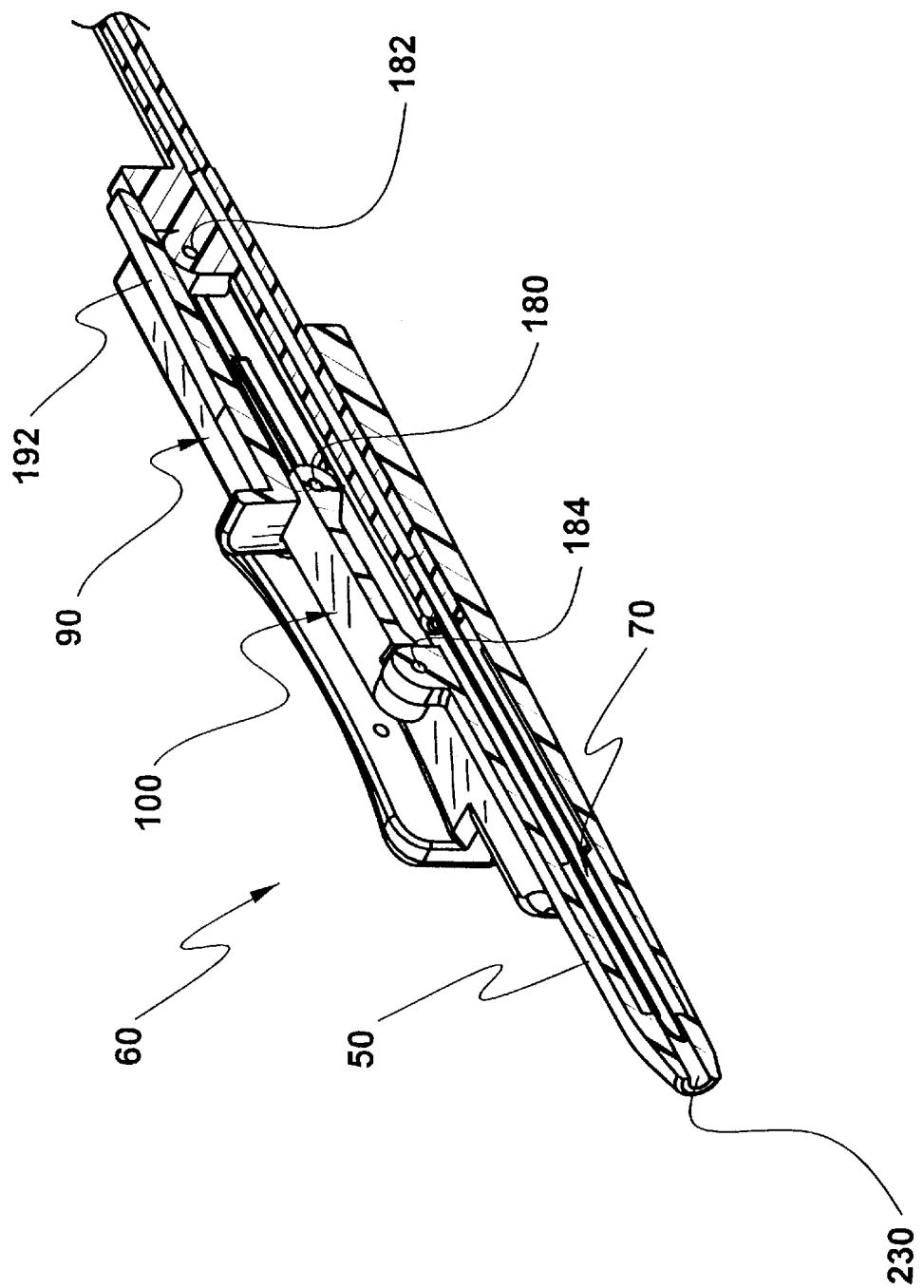
FIG. 6 is a cross section taken along lines 6—6 of the embodiment seen in FIG. 5.

Device 60 is seen in FIG. 5 to be at a state where needle 70 is fully retracted, enclosed and hidden within distal segment 50. Shaft 192 is returned to a non-stressed state. Arm 100 has pivoted about an angle of substantially 180° to so displace needle 70. Note that needle 70 is displaced approximately twice the length of arm 100. Also seen in FIG. 5 is one rail 198 of a pair of rails associated with needle hub assembly 30. The rails in cooperation with "U" shaped channel 110 restrain needle hub assembly 30 to slidable displacement in line with the long axis of needle 70. Safe containment of needle 70 within distal segment 50 is best seen in FIG. 6.

Figures 7, 8:
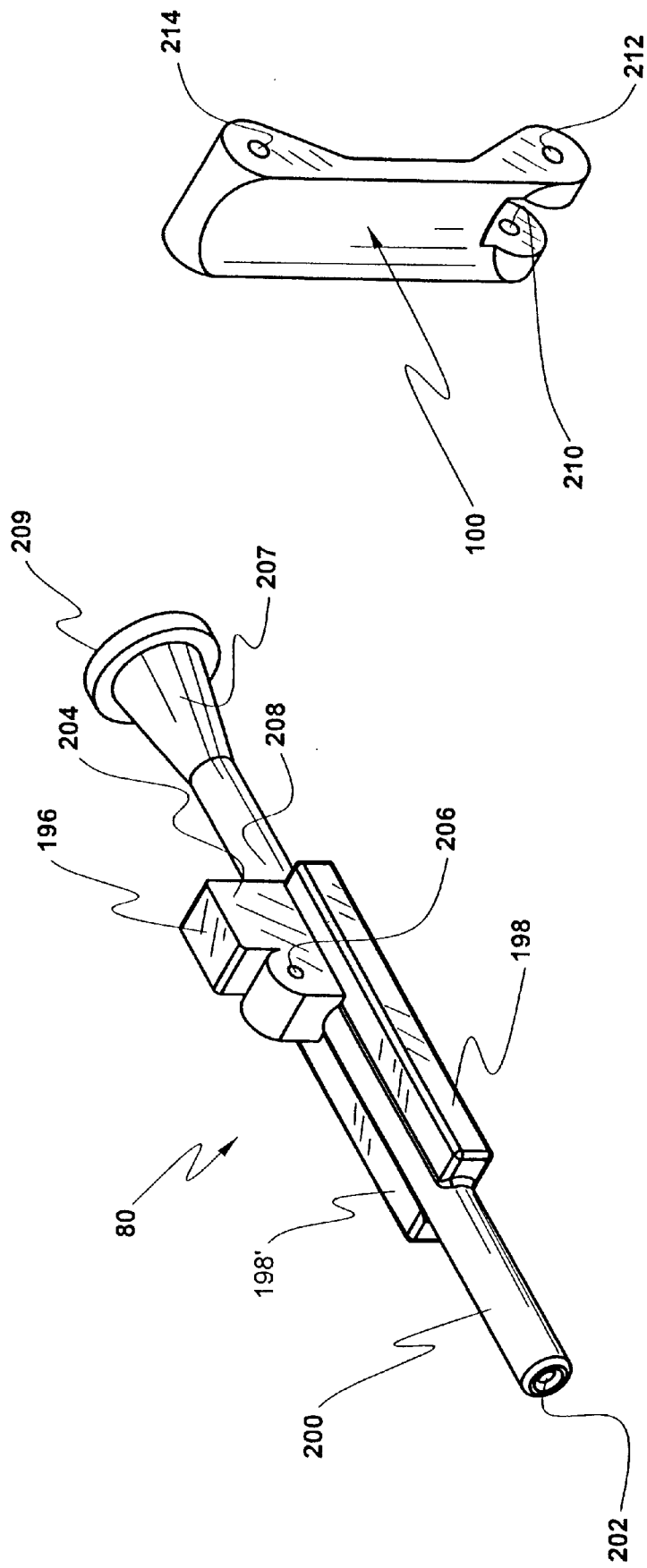
FIG. 7 is a needle hub portion of the device embodiment seen in FIG. 1.
FIG. 8 is a perspective of a first pivoting member of the device embodiment seen in FIG. 1.

Attention is now drawn to FIGS. 7–11 wherein needle hub 80, arm 100, arm 90 and body base part 122, respectively are seen as individual parts. Needle hub 80 is seen in FIG. 7 to comprise rail 198 and a juxtaposed rail 198'. Medially, hub 80 comprises an elongated hollow cylindrical part 200 wherein a needle 70 (not shown) is securely affixed within a distal orifice 202. Proximally, needle hub 80 comprises pedestal 204, a superior surface of which forms top smooth surface 196. A site 206 for hinge 182 is disposed near, but distal from pedestal 204. At the most proximal end, a fitting attachment 207 is disposed. Attachment 207 comprises an extension 208 which is contiguous with a luer fitting 209. Such fittings and attachments are well known in the art of medical connectors. While needle hub 80 may be made from a number of synthetic resinous materials, polyvinyl chloride is the current material of choice due to its strength, clarity and adhesive qualities.

Arm 100 is seen in FIG. 8. Arm 100 comprises sites 210 and 212 for hinge 184 and site 214 for hinge 180. The distance which separates sites 210 and 212 from 214 should be at least as long as one-half the length needle 70 extends outward from distal segment 50.

Figure 10:
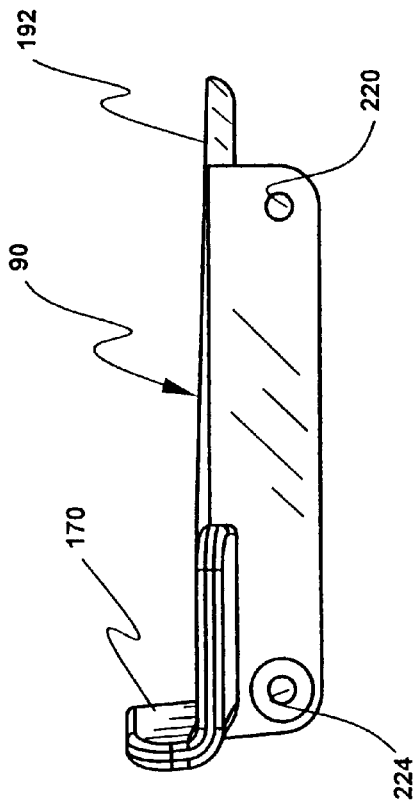
FIG. 10 is a side elevation of the second pivoting member seen in FIG. 9.
Figure 9:
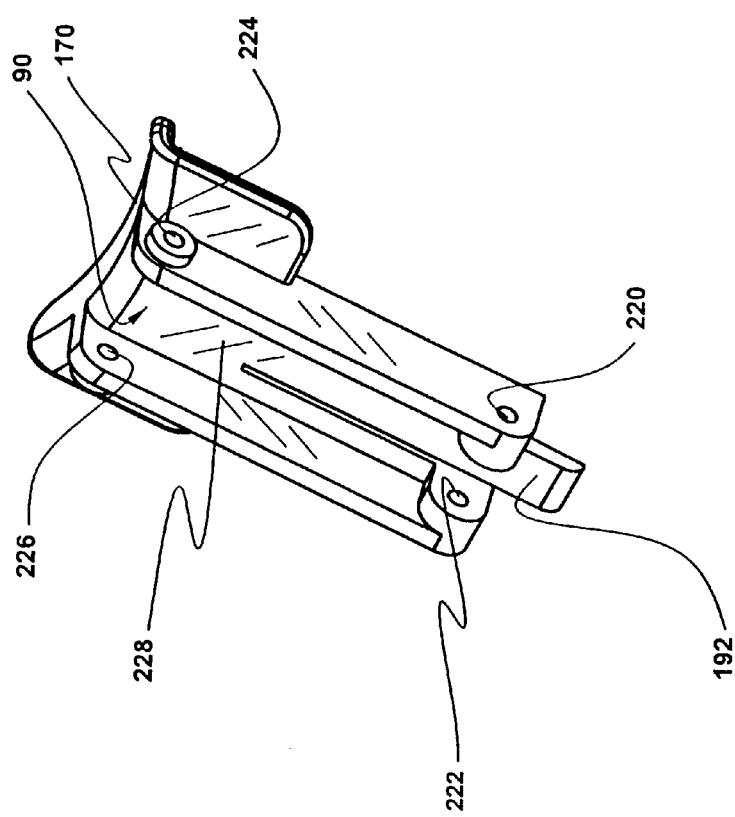
FIG. 9 is a perspective of a second pivoting member of a device which is similar to a second pivoting member of the device embodiment seen in FIG. 1, the differences being clearly enumerated hereafter.

Two different perspective views of arm 90 are seen in FIGS. 9 and 10. As earlier disclosed, arm 90 comprises an actuator tab 170 and a distortable shaft 192. In addition, arm 90 comprises sites 220 and 222 for hinge 182 and sites 224 and 226 for hinge 180. As the distance between sites 220/222 and 224/226 is greater than the distance which separates sites 210 and 212 from 214 (see FIG. 3), outward displacement of tab 170 to cause arm 90 to make an angle greater than 90° with base part 122 is not required to cause arm 100 to pivot through a 180° arc. Note that shaft 192 is formed as a cut-out of a larger planar section 228 (see FIG. 9) of arm 90. The extended length of shaft 192 must be great enough to rest upon surface 196 of hub 80 when shaft 192 is unstressed and to remain in contact with pedestal 204 at all times while being stressed as needle 70 is retracted.

Figure 11:
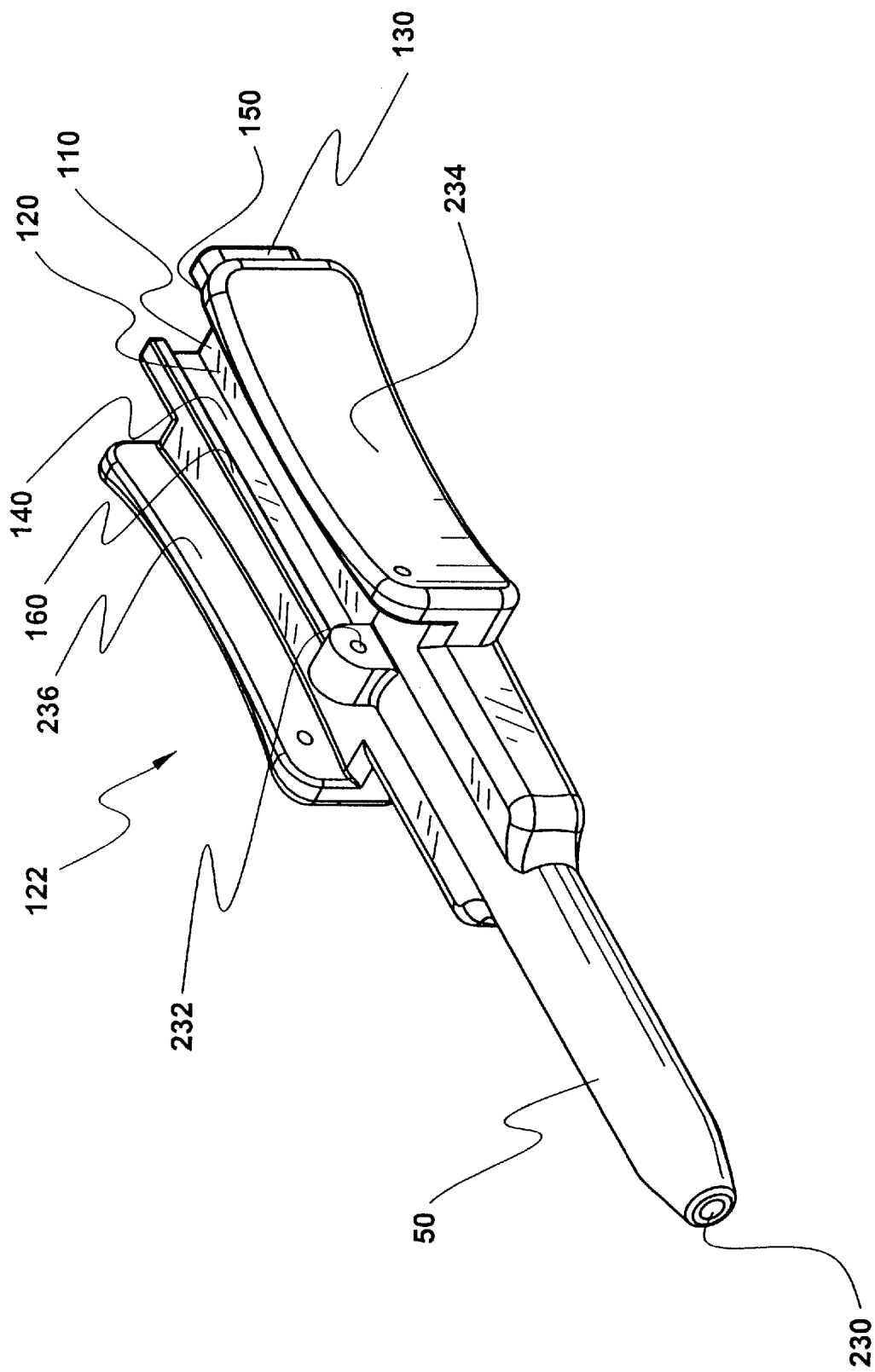
FIG. 11 is a perspective of a base portion of the device embodiment seen in FIG. 1.

Body base part 122 is seen in FIG. 11. As earlier disclosed, part 122 comprises distal segment 50 and "U" shaped channel 110. Part 122 also comprises a distal orifice 230 through which needle 70 is retracted, a site 232 for hinge 184 and a pair of juxtaposed handles 234 and 236 designed to meet the ergonomics of handling small needle percutaneous devices. Care should be taken to dispose handles 234 and 236 in a manner in which actuation of tab 170 is easy to accomplish with one digit of a hand (such as a forefinger while holding the device with the thumb and middle finger of the same hand. Of course, other disposition of such handles is possible within the scope of the instant invention. In some cases, handles may not be used or provided.

Even though device 60 is stable in both the extended needle and retracted needle states, achievement of desired safety suggests at least a permanent latch/catch mechanism be employed to assure a retracted needle shall not escape from confinement of distal segment 50. While other latch/catch mechanisms may be employed within the scope of the instant invention, one example of such mechanisms is provided in FIGS. 12–14.

Figure 12:
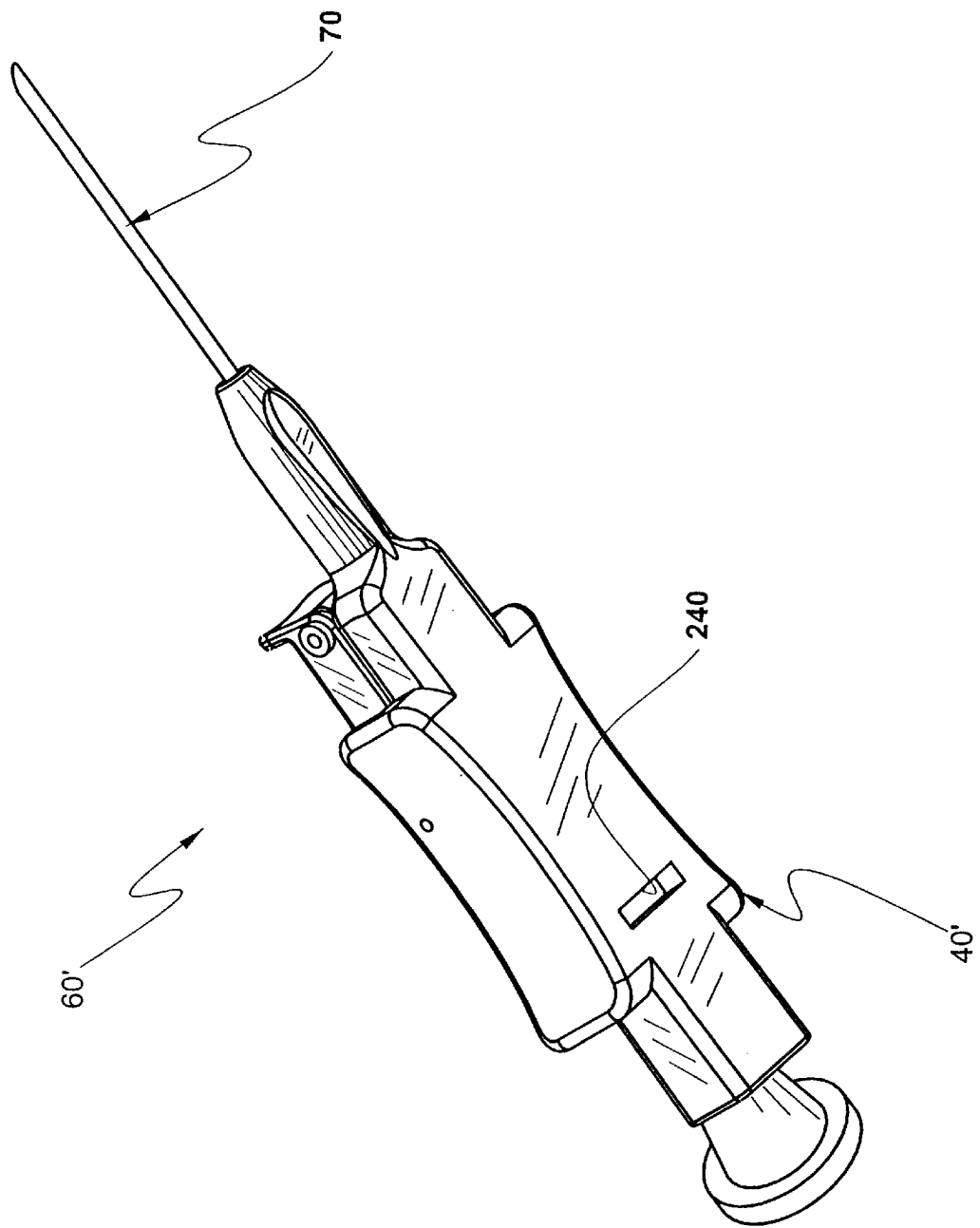
FIG. 12 is a perspective wherein the bottom of the base portion of FIG. 11 is clearly seen.

As seen in FIG. 12, body assembly 40' of a device 60' comprises a slit 240, through base section 120, which is essentially transverse to the direction of needle 70 retraction to act as a catch for a part of a retracting needle hub. While slit 240 is seen to be a through hole through base section 120, a blind groove on the inward side of base section 120 would suffice for the catch and would be unaccessible from the exterior of body assembly 40.

Figure 13:
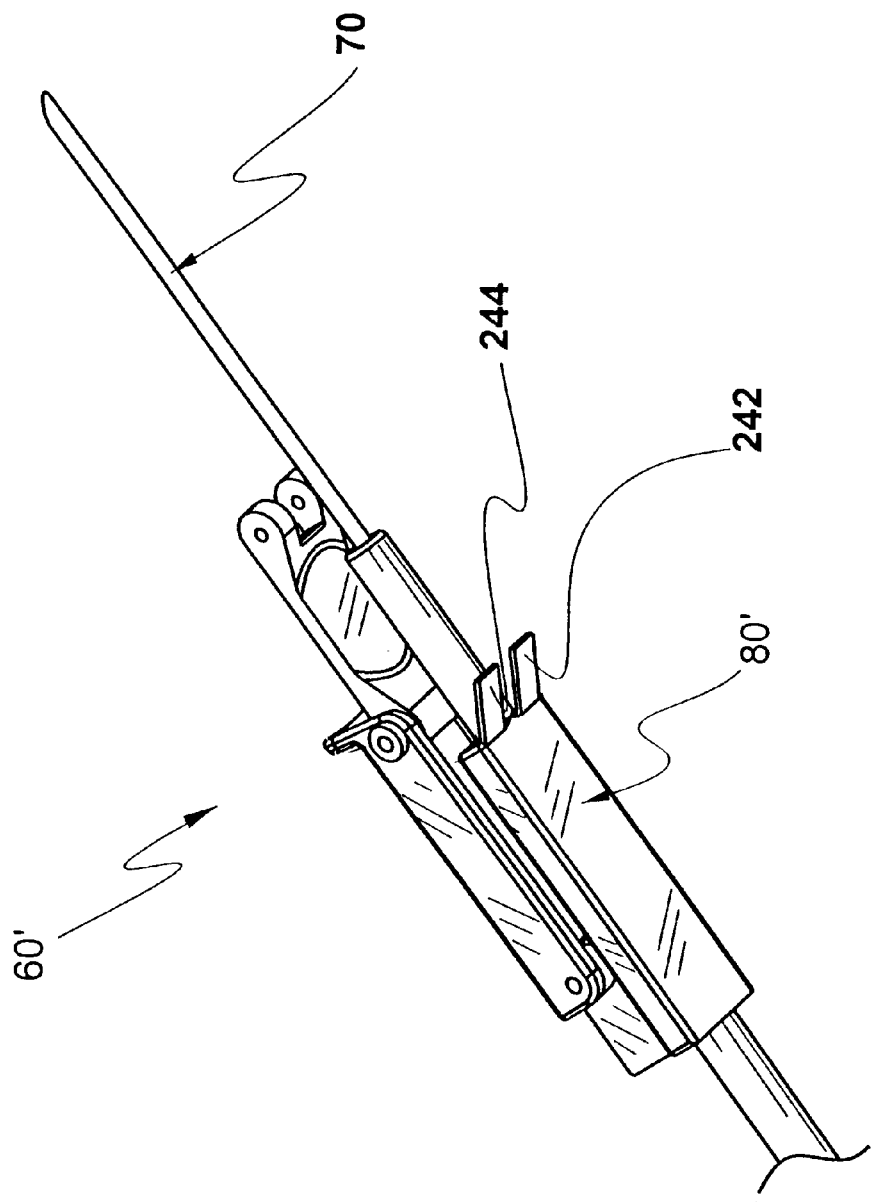
FIG. 13 is a perspective of the device embodiment seen in FIG. 1 with the base portion removed for visualizing locking tabs affixed to the needle hub portion and with the hub truncated.
Figure 14:
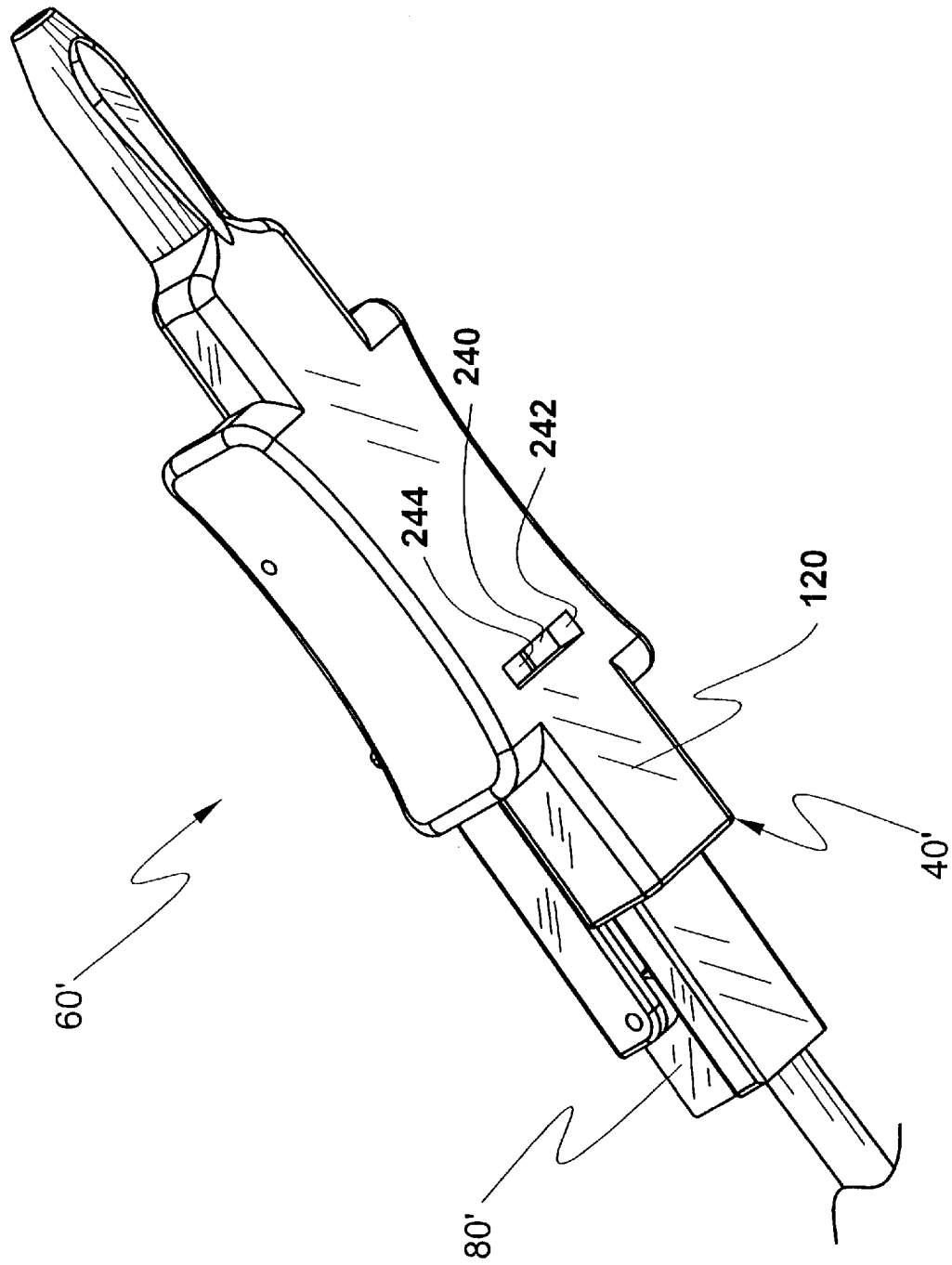
FIG. 14 is a perspective of the bottom of the device embodiment seen in 5 with the needle fully retracted and hub truncated.

Parts have been removed from body assembly 40' to permit a hub 80' to be clearly seen in FIG. 13. Hub 80' comprises a pair of latch tabs 242 and 244 which are molded or otherwise biased downward toward base section 120 (not seen in FIG. 13) when disposed thereby. Depending upon hub material used, it may be advisable to provide grooves in base section 120 which provide relief for tabs 242 and 244 while needle 70 is disposed for use in a catheter insertion procedure. As seen in FIG. 14, full retraction of needle hub 80' permits tabs 242 and 244 to latch into the catch provided by slit 240, thereby precluding any extension of needle 70 out of body assembly 40'.

Figure 15:
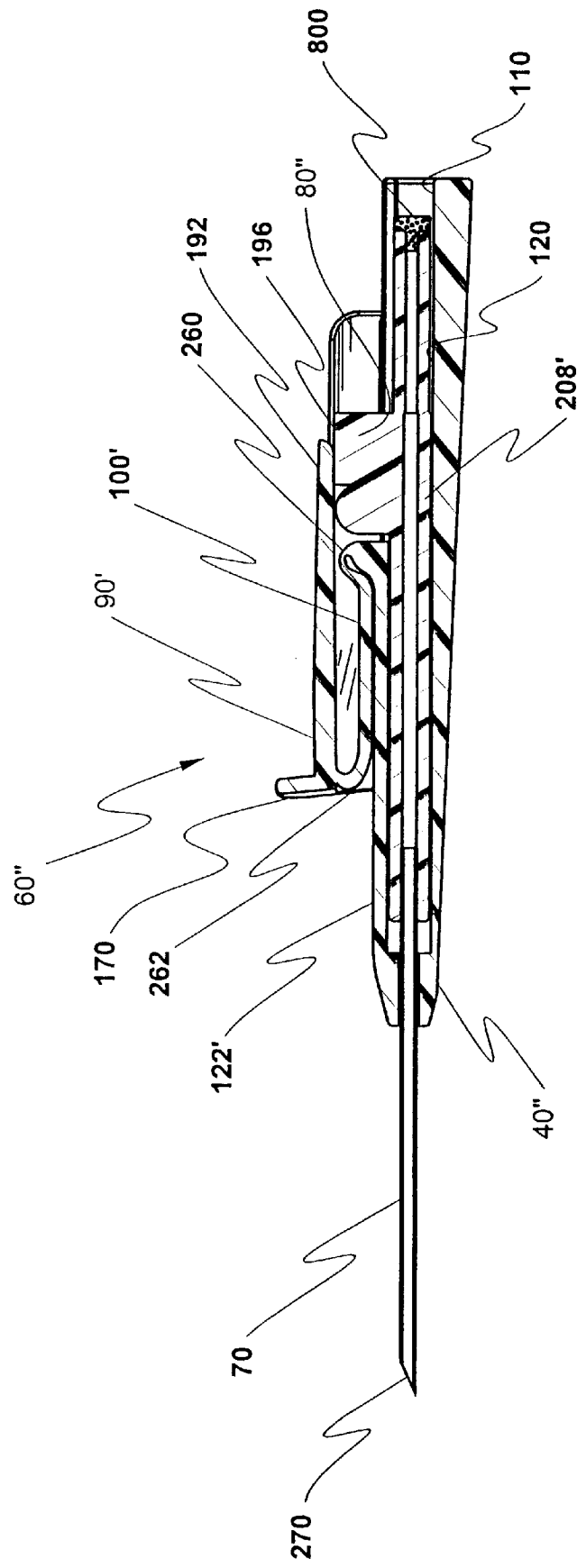
FIG. 15 is a cross section similar to the cross section seen in FIG. 3, but for another device embodiment of the invention wherein the base member and first and second pivoting members are joined by living hinges preferably formed within a single injection mold.
Figure 16:
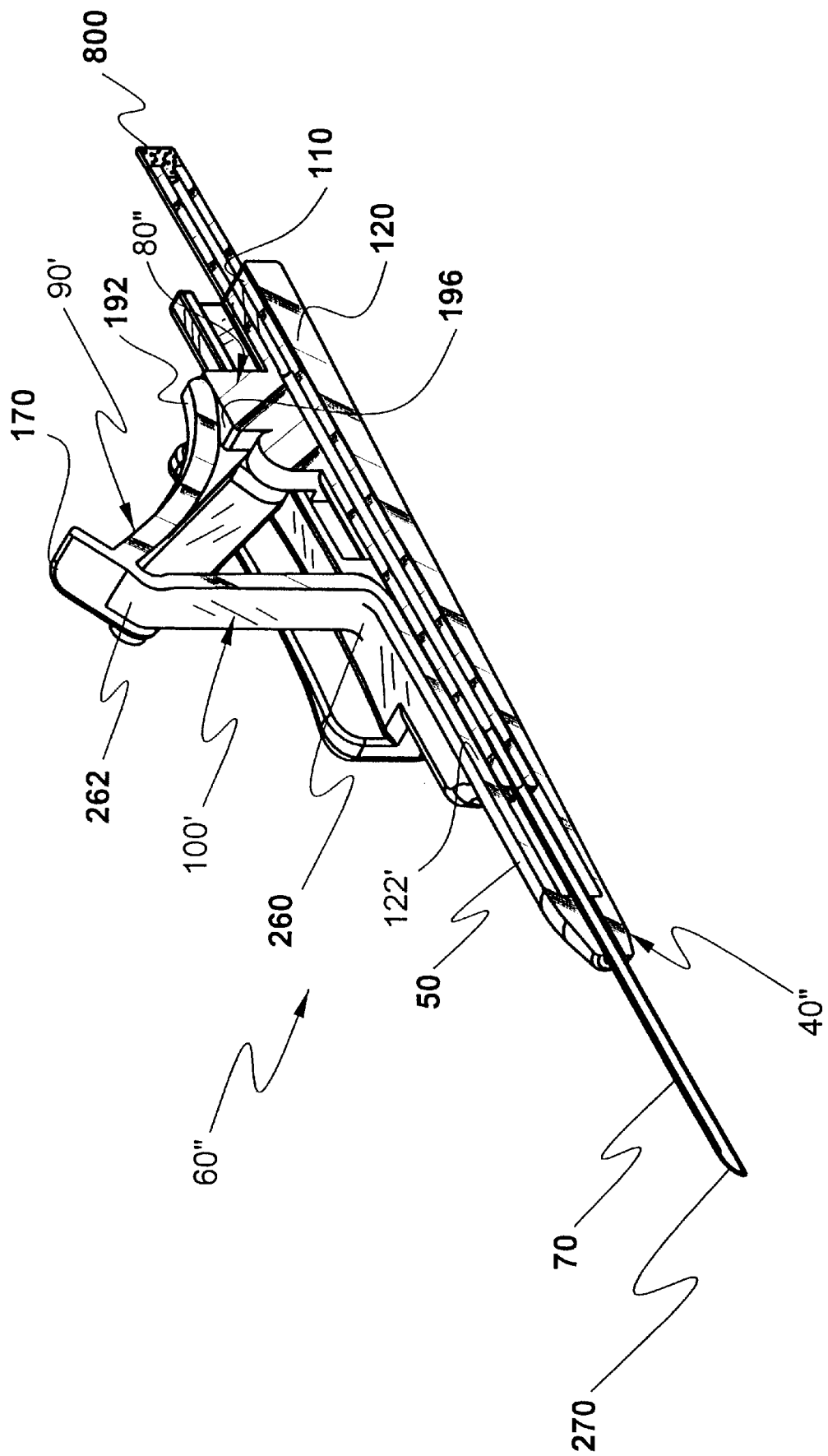
FIG. 16 is a cross section of a perspective, of the device embodiment seen in FIG. 15, wherein the needle is partially retracted.
Figure 17:
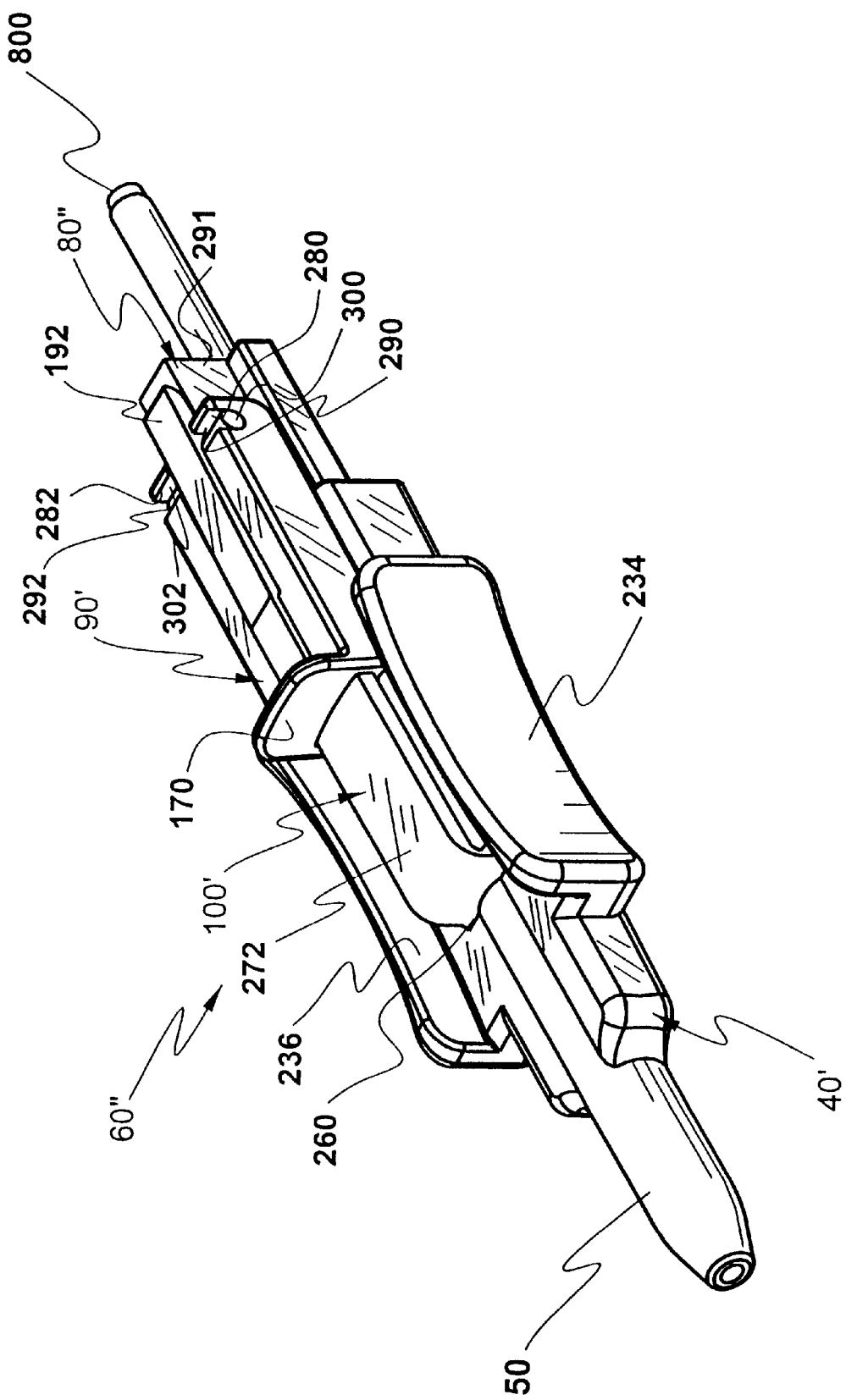
FIG. 17 is a perspective of the device embodiment, seen in FIGS. 15 and 16, wherein the needle is fully retracted.
Figure 18:
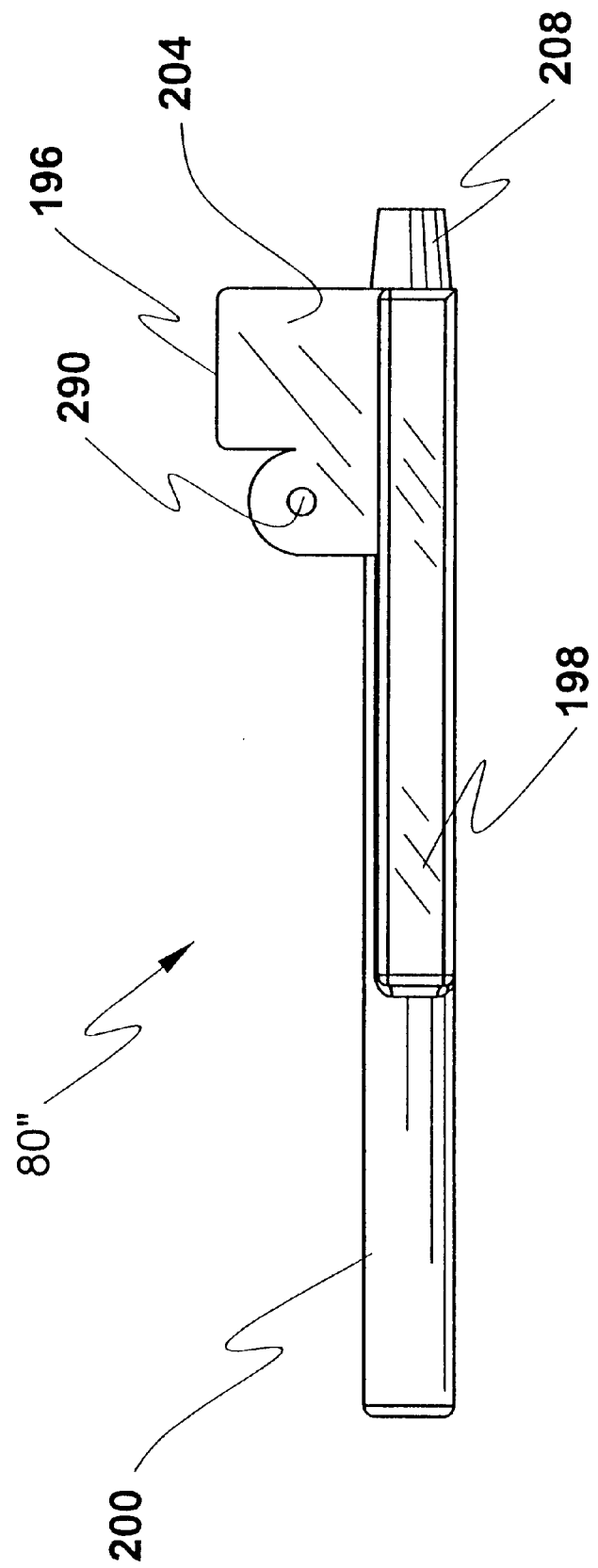
FIG. 18 is a side elevation of a hub part of the device embodiment seen in FIGS. 16, 17 and 18.

While devices 60 and 60' may be effectively used in a catheter insertion procedure, costs of producing the multiple numbers of parts (e.g. body part 122, arms 90 and 100 and hinges 180, 182 and 184) and assembling those parts into a complete body assembly (similar in function to body assembly 40 or 40') would likely make device 10 commercially unviable. However, through injection molding and use of appropriate material having clarity to see a flash chamber, rigidity to retract and safely restrain needle hub assembly 30 and flexibility to form useful living hinges permits all of a part providing the function of body assembly 40 or 40' to be made as a single injection molded part. Such a part (numbered 40") is seen in FIGS. 15–17. Note that device 60" performs the same functions as devices 60 and 60', but is fabricated from but two injection molded parts, body assembly 40" and needle hub 80".

As seen in FIG. 15, body assembly 40" comprises body part 122' (similar in form and function to body part 122) hingeably interconnected to an arm 100' through a living hinge 260. In similar fashion, an arm 90' is interconnected to arm 100' through a living hinge 262. Arm 90' also comprises a snap hinge connection to a needle hub 80" which is disclosed in detail hereafter. When the needle 70 is disposed for use in a catheter insertion procedure as seen in FIG. 15, arm 90' is compactly, horizontally folded in superior disposition relative to arm 100' which is also horizontally disposed to assure a compactness of device 60".

To retract needle 70 and its sharpened tip 270 into the safety of distal segment 50, tab 170 is pivoted proximally to displace arm 90' away from close juxtaposition with arm 100' as seen in FIG. 16. Note that arm 90', like arm 90, comprises a shaft 192 which is disposed to rest against top surface 196, of hub 80". As tab 170 is proximally pivoted, a hinged connection (disclosed in detail hereafter) between arm 90' and hub 80" urges hub 80" (and therefore needle 70 and needle tip 270 proximally) along "U" shaped channel 110. Such articulation of tab 170 also causes shaft 192 to be stressed as the distance between tab 170 and surface 196 is decreased by articulation of arm 90'. This stressing increases until arm 100' is rotated to be perpendicular relative to body part 122'. Once the point of perpendicularity is passed, the stress in shaft 192 is relieved with a subsequent release of energy stored in shaft 192 which forces arm 90, and tab 170 toward "U" shaped channel 110.

Once arms 90' and 100' are substantially parallel with base section 120, needle 70 and needle tip 270 are fully retracted into distal segment 50 for safe containment. Full retraction may be accomplished by release of force stored within shaft 192 or further enabled by application of digital force against tab 170 or alternatively against a superior revealed surface 272 of pivoted arm 100' (see FIG. 17). For facile operation, handles 234 and 236 may be displaced proximally and distally as ergonomic factors dictate.

Hinge connections 280 and 282 between arm 90' and hub 80" are seen in various parts and states in FIGS. 15–17. Best seen in FIG. 17, hinge connection 280 is seen to comprise a cylindrical post 290 affixed on a lateral side 291 of hub 80" which is sized and disposed to be snugly contained in a circular slot 300 disposed in arm 90'. Similarly, a hinge connection 282 comprises a cylindrical post 292 and a circular slot 302, juxtaposed on an opposite side of hub 80". Note that "U" shaped channel 110 in combination with hinge connections 280 and 282 securely maintain hub 80" for slidable displacement within channel 110. Disposition of post 290 on hub 80" is better seen in FIG. 18.

Figure 19:
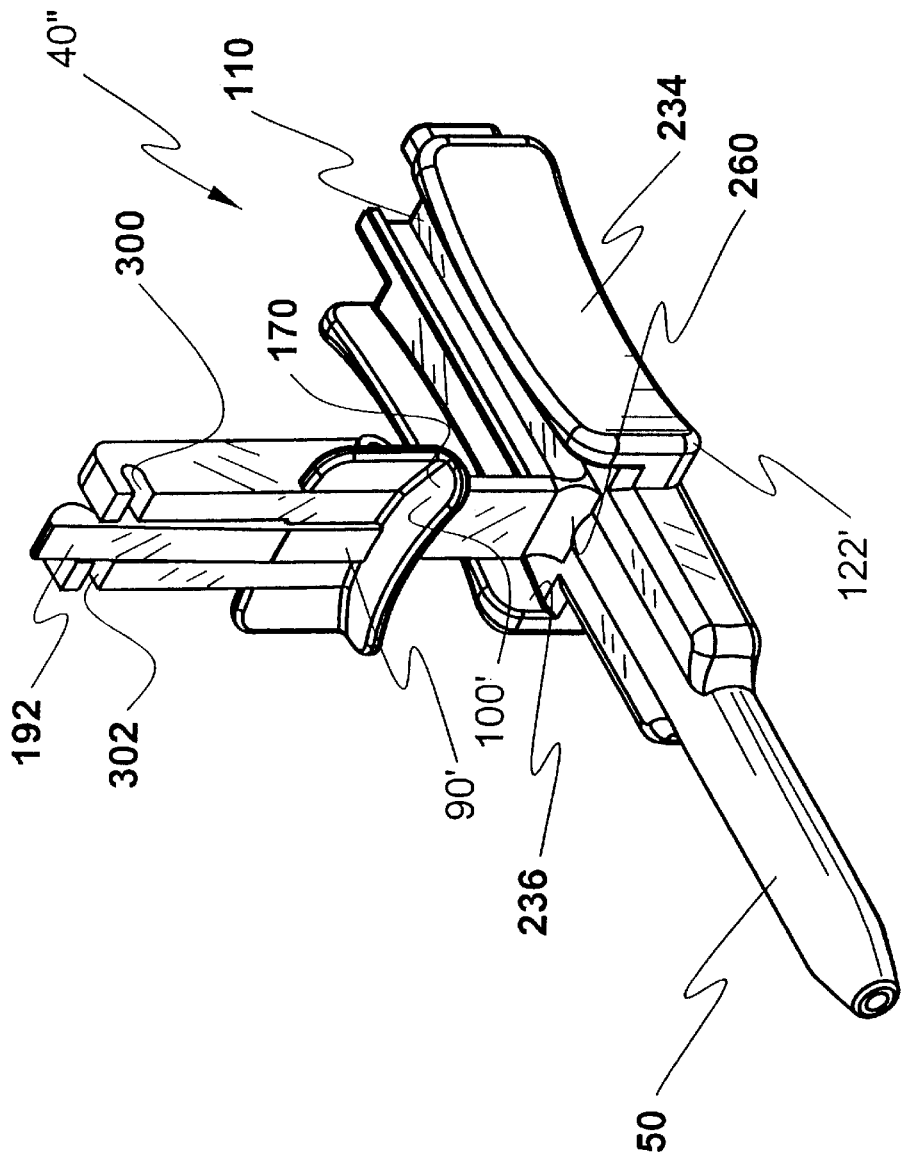
FIG. 19 is a perspective of a single molded part which may be used in the device embodiment seen in FIG. 15, the part comprising a base member and first and second pivoting members.

An example of body assembly 40" in an as molded state is seen in FIG. 19. Arms 90' and 100' are molded essentially in-line, orthogonal to body part 122'. In this manner, circular slots 300 and 302 are open to a horizontal mold pull. Note that pivoting arm 90' through a near 180° arc and then, while holding arm 100' essentially vertical or orthogonal, inserting hub 80" into "U" shaped channel 110 until arm 90"'gives" to permit insertion of posts 290 and 292 into slots 300 and 302,respectively, securely affixes hub 80" to arm 90' within "U" shaped channel 110 through all positions in which hub 80" is displaced in needle 70 extension and retraction. Body assembly 40"' is preferably molded as a single part from polypropylene, although other synthetic resinous materials may be used within the scope of the invention.

Figure 20:
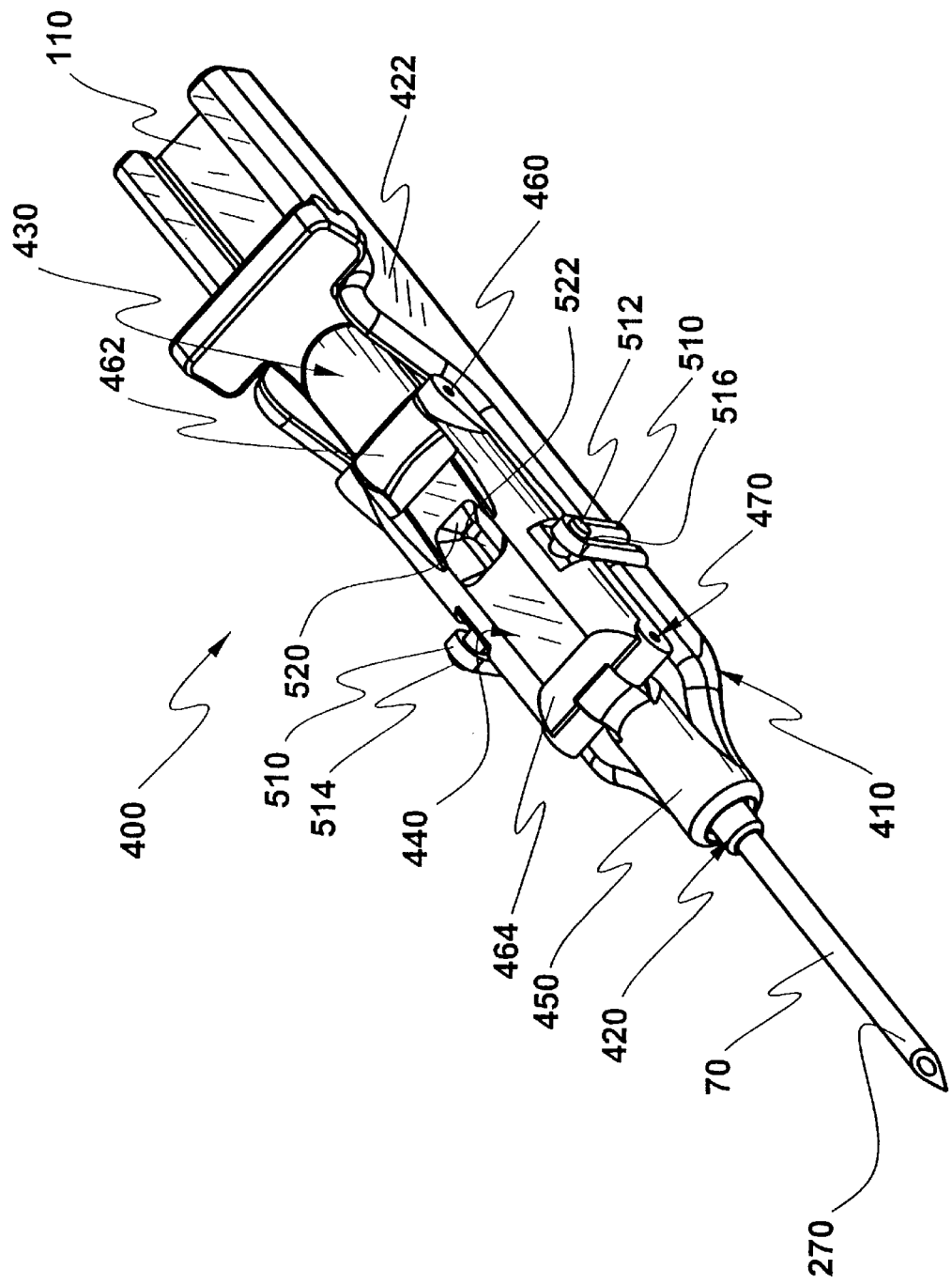
FIG. 20 is a perspective of yet another embodiment, this embodiment being seen without a catheter.
Figure 21:
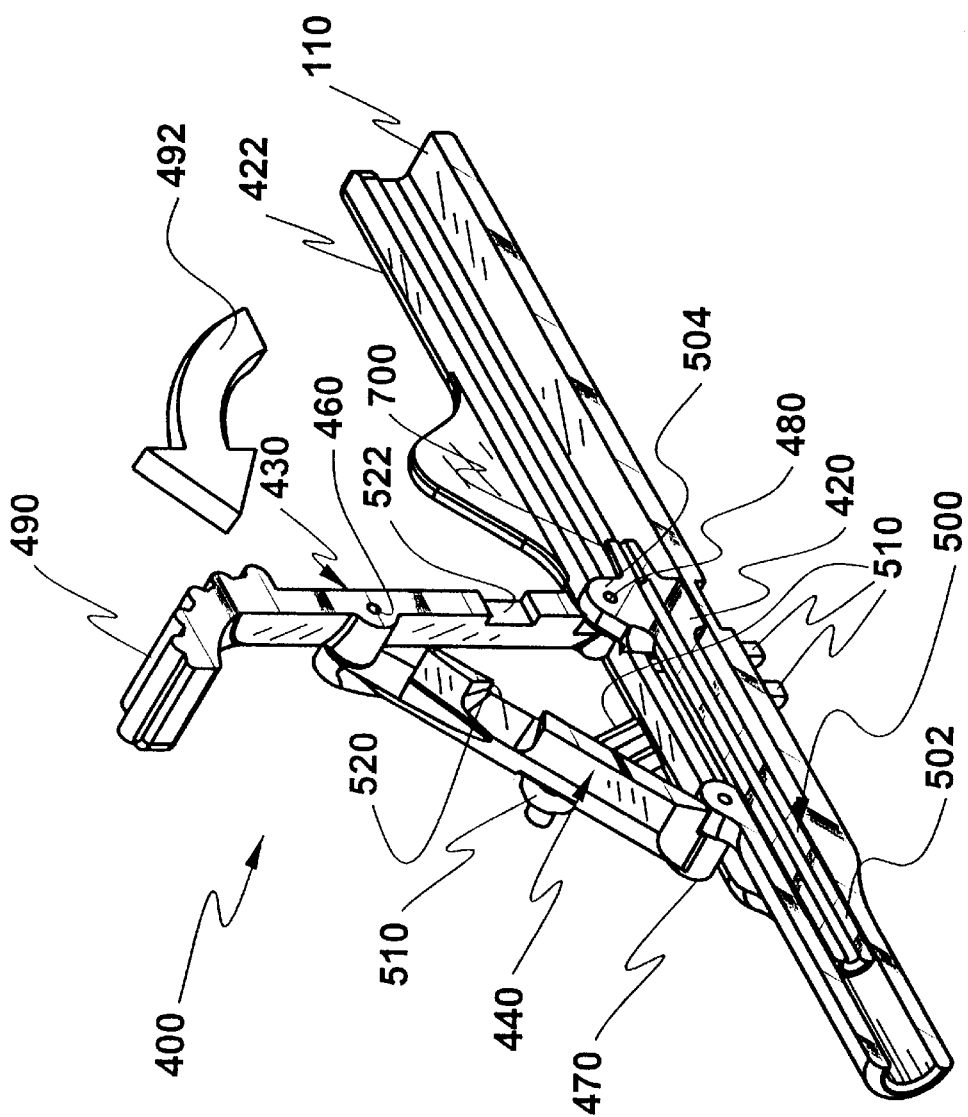
FIG. 21 is a lengthwise cross section of a perspective of the device embodiment, seen in FIG. 20, wherein the device is disposed in a mode wherein a needle (not seen in FIG. 21) affixed thereto would be partially retracted.
Figure 22:
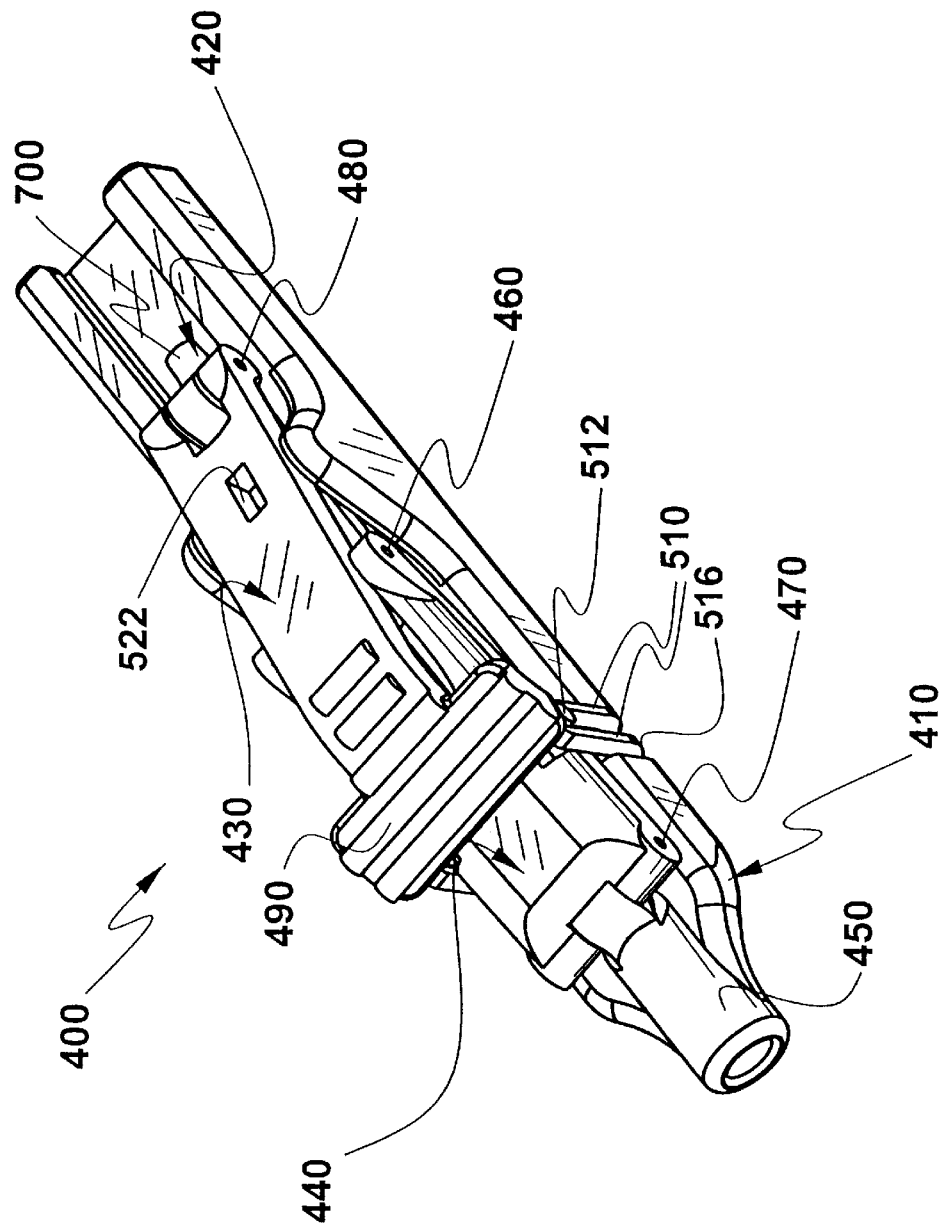
FIG. 22 is a perspective of the device embodiment, seen in FIG. 21, wherein the device is disposed in a mode wherein a needle affixed thereto would be fully retracted.

As seen in FIGS. 20–22, device 400 represents another embodiment of the invention. Similar to the device embodiments 60, 60' and 60", device 400 is an in-line, small bore needle safety retraction device. To permit more detail in presentation, the catheter insertion needle is removed in FIG. 21. Also no needle cover, such as cover 20, seen in FIG. 1, is shown in FIGS. 20–22, though such covers are commonly used to protect needle tips during transport and storage prior to use.

Referring to FIG. 20, device 400 is seen to comprise a body assembly 410 and a needle hub assembly 420, which is seen only in part after removal of the needle cover. Body assembly 410, similar to body base part 122 of body assembly 40, comprises a body base part 422 and two arms, 430 and 440, which are pivoted to retract a catheter insertion needle 70 and its associated sharpened tip 270 into a safety enclosure afforded by a distal section 450 of body assembly 410. Similar to base body part 122 of body assembly 40, body base part 422 comprises a "U" shaped channel, which is also referenced by 110 and which provides slidable containment of needle hub assembly 420.

Arm 430 comprises a medially disposed hinge connection 460 to a proximal end 462 of arm 440. On a distal end 464, arm 440 further comprises a hinge connection 470 to body base part 422. As is clearly seen in FIG. 21, arm 430 comprises a hinge connection 480 which is initially distally disposed relative to hinge connection 460 while needle 70 is disposed for use in a catheter insertion procedure. Arm 430 also comprises a needle retraction actuation tab 490 which is proximally disposed while needle 70 is disposed for use in the catheter insertion procedure and which is displaced away from body base part 422 in the direction of arrow 492 to cause needle 70 to retract into body base part.

Needle hub assembly 420 comprises a needle hub 500 and catheter insertion needle 70 with sharpened tip 270 (not seen in FIG. 21). Needle hub 500 comprises an elongated distal nose section 502 into which a proximal end of needle 70 is securely affixed and a proximal hinge connection part 504 by which arm 430 is hingeably affixed to hub 500 such that when arm 430 is pivoted about hinge 460 hub 500 and needle 70 are proximally displaced.

Needle hub assembly 420 is totally retracted into safety of confinement of needle 70 and needle tip 270 into distal section 450 by outward and then inward pivoted displacement of tab 490. The first position (for catheter insertion use) of arm 430 is seen in FIG. 20. A medially disposed pivoted arm 430 is seen in FIG. 21 and a completely rotated arm 430 is seen in FIG. 22. Attention is now drawn to FIG. 20 wherein an elastic band 510 is seen to be disposed about a pair of horizontally disposed pegs 512 and 514 and further about a channel 516 in body base part 422. Note that elastic band 510 is relatively unstressed while device 400 is disposed for use in the catheter insertion procedure. It is stretched to store energy as arm 440 is displaced away from body base part 422 as a result of tab 490, and arm 430, (see FIG. 21) being outwardly displaced. Then, as tab 490 is pivoted distally until arm 430 rotates to form an acute angle relative to body base part 422, the energy stored in elastic band 510 urges arm 440 and therefore arm 430 to complete articulation and close upon body base part 422. Note that, in this case, arm 430 has proceeded from a position which was inferior to arm 440 to become disposed in a superior relation thereto. In this manner, device 400 provides a power assist to complete safety retraction of needle 70 and its sharpened tip 270 into distal section 450.

Attention is again drawn to FIG. 20 wherein a pair of in-line slots 520 and 522, disposed in arms 440 and 430, respectively. These in-line slots provide a free optical pathway to visualize tubing affixed to needle hub assembly 420 (see FIG. 21) for an early indication of blood flash as needle tip 270 enters a blood vessel.

Note that needle hub assembly 420, comprises a proximal hub 700 which serves as a fitting attachment, which may be used to affix a removable liquid/gas separator valve. Heretofore, reference has been made to a blood flash. Early visualization of access to a blood vessel is a common and practical method for determination of vessel entry. To permit such visualization without undue blood discharge, a liquid/gas separator valve which permits gas emission while retaining liquids is generally disposed at the proximal end of a blood flow channel, such as flow channel 750, disposed in hub 80 (best seen in FIG. 3). Such a separator valve 760 is seen to be affixed to proximal hub 700 through an elongated hollow extension 770. For convenience, separator valve 760 may comprise a luer fitting 780 into which a plug 790 is securely, but releasibly, affixed. Plug 790 may be made from any material which passes gas while retaining liquid, such as Goretex. It should be noted that hub 80 and extension 770 and fitting 780 may be made as a single molded part to reduce cost of manufacture. A different liquid/gas separator plug 800 is seen in FIGS. 15–17. Plug 800 is disposed within a portion of a hub 208' which has no connection to a luer fitting or other fluid communicating parts; however, use of plug 800 is such a mode decreases length of device 60".

Generally, the needle hubs may be made from polyvinyl chloride. Each inter arm hinge (from the group of hinges numbered 180, 260 and 460) may be a living hinge formed as a molded part of so interconnected, associated arms. Each arm-to-base part hinge (from the group of hinges numbered 184, 470 and 632) may also be living hinges formed as a molded part of so interconnected arm and base parts. In this manner all base and arm parts for a particular device may be fabricated from a single injection molded part of a synthetic resinous material such as polypropylene.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A safety catheter insertion needle retracting device comprising:

a needle hub assembly comprising a needle hub and a catheter insertion needle securely affixed at a proximal end thereof to a distal portion of the needle hub, said catheter insertion needle having a sharpened tip on its distal end and an elongated cannula disposed along a longitudinal axis of said hub assembly between the sharpened tip and the proximal end, said hub portion comprising a through hole in line with said cannula for providing a communicating fluid pathway there through;

a catheter releasibly affixed about said catheter insertion needle;

an elongated body assembly in which said needle hub assembly is slidably affixed, said elongated body assembly comprising a distal part, which is proximally disposed relative to said sharpened tip during the catheter insertion procedure and which surrounds and encloses said sharpened tip when the needle is retracted, and a proximal part which comprises a guide path through which a proximal portion of said needle hub is confined to glide proximally as said needle is retracted; and said body assembly further comprising a pair of substantially rigid elongated parts each of which is hingeably affixed to the other, one end of one of the pair of parts being hingeably affixed to said elongated body part and the other being hingeably affixed to the needle hub such that the parts pivot in line with said longitudinal axis, with one of said parts rotating approximately 180° to urge retraction of said needle hub and catheter insertion needle from an extended state to a retracted state whereat said needle tip is enclosed within the distal part.

2. The safety catheter insertion needle retracting device according to claim 1 further comprising a releasibly affixed needle cover which is removed to bare the needle for use in the catheter insertion procedure.

3. The safety catheter insertion needle retracting device according to claim 1 wherein one of said rigid elongated parts further comprises a distortable part which is stressed to store energy during a first portion of a needle retraction and which responsively releases the stored energy during a subsequent portion of needle retraction to assist completion of needle retraction.

4. A safety catheter insertion needle retraction device for use in percutaneous catheter insertion procedures, said device comprising:

a needle enclosure housing assembly comprising:

a slender, elongated base part comprising an extended longitudinal axis and a planar slide channel for a needle hub assembly, said slide channel being disposed in-line with the longitudinal axis;

a first substantially rigid, elongated pivoting part;

a second substantially rigid, elongated pivoting part;

a first hinge connection adjoining one end of said first pivoting part to said second pivoting part such that articulation of the first and second parts is in line with the longitudinal axis of the elongated base part;

a second hinge connection adjoining said base part to said first pivoting part at an end opposite the one end such that articulation of the first part is in line with the longitudinal axis of the base part;

a needle hub assembly slidably disposed within said slide channel and comprising:

a catheter insertion needle comprising an elongated, hollow bore cannula defining a long axis of said needle hub assembly, said cannula having a sharpened tip disposed at a distal end and a proximally disposed end;

a needle hub comprising a through borehole disposed in alignment with said long axis and securely affixed at a distal end to the proximally disposed e nd of said cannula and a distally disposed hub whereat a fluid flow apparatus is affixed for use in catheter insertion procedures; and a third hinge connection disposed to hingeably affix said second pivoting part to said hub such that articulation of said second part is in line with the longitudinal axis of the base part;

said pivoting parts and assemblies cooperating to fold into a first stable state such that the device has the characteristics of a compact, slender, low silhouette, catheter insertion implement when said catheter insertion needle is disposed for use in a catheter insertion procedure, further cooperating to retract said needle hub assembly as said pivoting parts are rotated away from said elongated base part and, upon rotating one of the pivoting parts substantially 180° to fold said pivoting parts and assemblies cooperatively to a second stable state, thereby slidably retracting said hub along said slide channel to fully enclose said sharpened t tip within a distal portion of said needle enclosure housing assembly.

5. The safety catheter insertion needle retraction device according to claim 4 wherein said hub comprises a latch and said needle enclosure housing assembly comprises a catch disposed to securely affix said hub when fully retracted to permanently enclose said needle tip.

6. The safety catheter insertion needle retraction device according to claim 4 wherein said first and second hinges are living hinges formed as part of a single injection molded part comprising said pivoting parts and said needle enclosure housing assembly.

7. The safety catheter insertion needle retraction device according to claim 4 further comprising a needle cover which is disposed to shield said needle tip during shipment and storage and removed for access to said needle during a catheter insertion procedure.

8. The safety catheter insertion needle retraction device according to claim 4 wherein said elongated base part and needle hub assembly cooperatively each comprise a blood flash visualization section disposed proximally from said proximally disposed end of said cannula.

9. The safety catheter insertion needle retraction device according to claim 4 wherein said elongated base part comprises a pair of laterally juxtaposed handles.

10. The safety catheter insertion needle retraction device according to claim 4 wherein said slide channel comprises a "U" shaped channel formed from planar base, adjoining vertical side walls having inwardly biased lips at the top thereof.

11. The safety catheter insertion needle retraction device according to claim 4 wherein the cooperating pivoting parts and assemblies comprise means for rotating said second pivoting arm 180° to fully retract and enclose said needle tip.

12. The safety catheter insertion needle retraction device according to claim 4 wherein the cooperating pivoting parts and assemblies comprises means for rotating said first pivoting arm arm 180° to fully retract and enclose said needle tip.

13. The safety catheter insertion needle retraction device according to claim 4 wherein said second pivoting arm comprises an actuator tab disposed on a proximal end thereof.

14. The safety catheter insertion needle retraction device according to claim 4 wherein said second pivoting arm comprises an actuator tab disposed on a distal end thereof.

15. The safety catheter insertion needle retraction device according to claim 4 wherein said second pivoting arm comprises an elastic member which stores energy as the second pivoting arm is outwardly displaced to initiate needle retraction and releases energy to urge the needle and needle tip into fully shielded enclosure as the second pivoting arm is inwardly displaced.

16. The safety catheter insertion needle retraction device according to claim 4 wherein said needle enclosure housing assembly comprises an elastic band disposed between said elongated base part and the first pivoting arm which stores energy as the first pivoting arm is outwardly displaced to initiate needle retraction and releases energy to urge the needle and needle tip into fully shielded enclosure as the first pivoting arm is inwardly displaced.

17. The safety catheter insertion needle retraction device according to claim 4 wherein said third hinge comprises means for snapping the corresponding hinged parts together.

18. A safety catheter insertion needle retracting device comprising:
- an elongated body assembly comprising a slide containment channel for a needle hub and a distal enclosure for safely enclosing an associated retracted catheter insertion needle;
- the needle hub and associated catheter insertion needle being slidably disposed in said containment channel, said needle hub being securely affixed to the catheter insertion needle, said needle comprising a distally disposed sharpened tip for percutaneous entry and a long axis direction in line with said hub and said sharpened tip; and
- said body further comprising a needle retraction actuator which is a part of a communicating link between said hub and said body, said actuator being angularly displaced away from the rest of said device with a linear displacement along said long axis to urge said catheter insertion needle and said sharpened tip to travel a sufficient distance to fully retract said sharpened tip into said enclosure, the displacement of said actuator being a shorter distance than the travel distance of the sharpened tip.

19. A method for retracting a catheter insertion needle into safe confinement comprising the steps of:
- providing a safety catheter insertion needle retracting device comprising:
  - a needle hub assembly comprising a needle hub and a catheter insertion needle securely affixed at a proximal end thereof to a distal portion of the needle hub, said catheter insertion needle having a sharpened tip on a distal end and an elongated cannula disposed along a longitudinal axis of said hub assembly between the sharpened tip and the proximal end, said hub portion comprising a through hole in line with said cannula for providing a communicating fluid pathway there through;
  - an elongated body assembly in which said needle hub assembly is slidably affixed, said elongated body assembly comprising a distal part, which is proximally disposed relative to said sharpened tip during the catheter insertion procedure and which surrounds and encloses said sharpened tip when the needle is retracted, a proximal part, which comprises a guide path through which a proximal portion of said needle hub is confined to glide proximally as said needle is retracted, and a pair of substantially rigid elongated parts each of which is hingeably affixed to the other, one end of one of the pair of parts being hingeably affixed to said elongated body part and the other being hingeably affixed to the needle hub such that the parts pivot in line with said longitudinal axis, with one of said parts rotating approximately 180° to urge retraction of said needle hub and catheter insertion needle from an extended state to a retracted state whereat said needle tip is enclosed within the distal part;
- initiating needle retraction through a mechanical advantage derived from outwardly pivoting said pivotal parts; and
- rotating one of said pivotal parts substantially 180° to completely retract and enclose the needle.

20. The method according to claim 19 wherein the rotating step comprises rotating the one of said pivotal parts distally.

21. The method according to claim 19 wherein the rotating step comprises rotating the one of said pivotal parts proximally.

* * * * *